United States Patent
Cheung et al.

(10) Patent No.: US 12,364,752 B2
(45) Date of Patent: Jul. 22, 2025

(54) METHODS OF ENHANCING IMMUNOGENICITY OF POORLY IMMUNOGENIC ANTIGEN-SPECIFIC VACCINES USING ORAL YEAST BETA-GLUCANS

(71) Applicant: Memorial Sloan Kettering Cancer Center, New York, NY (US)

(72) Inventors: Nai-Kong Cheung, New York, NY (US); Shakeel Modak, New York, NY (US); Govind Ragupathi, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1053 days.

(21) Appl. No.: 17/049,759

(22) PCT Filed: Apr. 23, 2019

(86) PCT No.: PCT/US2019/028813
§ 371 (c)(1),
(2) Date: Oct. 22, 2020

(87) PCT Pub. No.: WO2019/209890
PCT Pub. Date: Oct. 31, 2019

(65) Prior Publication Data
US 2021/0236630 A1    Aug. 5, 2021

Related U.S. Application Data

(60) Provisional application No. 62/662,176, filed on Apr. 24, 2018.

(51) Int. Cl.
*A61K 9/00* (2006.01)
*A61K 39/00* (2006.01)
(Continued)

(52) U.S. Cl.
CPC ...... *A61K 39/39* (2013.01); *A61K 39/001171* (2018.08); *A61P 35/00* (2018.01);
(Continued)

(58) Field of Classification Search
CPC ............... A61K 39/00; A61K 39/39; A61K 39/001171; A61K 2039/00;
(Continued)

(56) References Cited

U.S. PATENT DOCUMENTS 7,704,973 B2 * 4/2010 Cheung ............... A61P 43/00
536/123.12
2006/0160766 A1 7/2006 Cheung
(Continued)

FOREIGN PATENT DOCUMENTS

| | | |
|---|---|---|
| JP | 2009-528267 A | 8/2009 |
| WO | WO-2007/084661 A2 | 7/2007 |
| WO | WO-2017/027568 A1 | 2/2017 |

OTHER PUBLICATIONS

De Smet et al, Human Vaccines & Immunotherapeutics, vol. 10, No. 5, pp. 1309-1318 (Year: 2014).*
(Continued)

*Primary Examiner* — Paul W Dickinson
(74) *Attorney, Agent, or Firm* — Foley & Lardner LLP

(57) ABSTRACT

The present disclosure provides methods for enhancing the immunogenicity of a poorly immunogenic antigen-specific vaccine as well as methods for promoting diversification of the gut microbiome in a subject in need thereof comprising administering to the subject an effective amount of a beta-glucan extract derived from yeast. Kits for use in practicing the methods are also provided.

12 Claims, 31 Drawing Sheets

(51) Int. Cl.
  *A61K 39/39* (2006.01)
  *A61P 35/00* (2006.01)
(52) U.S. Cl.
  CPC .............. *A61K 2039/5152* (2013.01); *A61K 2039/55583* (2013.01); *A61K 2039/6081* (2013.01)
(58) Field of Classification Search
  CPC .. A61K 2039/55583; A61K 2039/6081; A61K 2039/5152; A61K 2039/55577; A61K 2039/575; A61K 39/12; A61K 31/00; A61K 31/716; A61K 2300/00; A61P 35/00; A61P 31/00; A61P 31/16; C07K 16/2812; C07K 16/2887; C07K 16/3084; C07K 2317/73; C12N 2760/16134; Y02A 50/30
  USPC .......... 424/1.11, 1.49, 1.57, 1.65, 1.69, 1.73, 424/9.1, 9.2
  See application file for complete search history.

(56) References Cited

U.S. PATENT DOCUMENTS

| | | |
|---|---|---|
| 2009/0053221 A1 | 2/2009 | Cheung et al. |
| 2016/0213702 A1 | 7/2016 | Von Maltzahn et al. |

OTHER PUBLICATIONS

Krug et al, Clinical Cancer Research, vol. 10, No. 18, Part 1, pp. 6094-6100 (Year: 2004).*

Spencer, Immunotherapy for Alzheimer's disease: past, past, present, and future; Frontiers in Aging Neuroscience, 2014, 6, 114, p. 1-6 (Year: 2014).*

Helling et al., "Ganglioside conjugate vaccines," Molecular and Chemical Neuropathology, vol. 21, pp. 299-309 (Feb. 1994).

International Search Report and Written Opinion, PCT/US2019/028813, Memorial Sloan Kettering Cancer Center (Aug. 30, 2019).

Luo et al., "Yeast-derived β-1, 3-glucan substrate significantly increased the diversity of methanogens during in vitro fermentation of porcine colonic digesta," J. Integrative Agriculture, 12(12), pp. 2229-2234 (Dec. 19, 2012).

Kushner et al: "Phase I Trial a Bivalent Gangliosides Vaccine in Combination with β-Glucan for High-Risk Neuroblastoma in Second or Later Remission", Clinical Cancer Research, vol. 20, No. 5, Feb. 11, 2014 (Feb. 11, 2014), pp. 1375-1382.

Le Thanh Hoa et al: "Adjuvant effects of Sophy [beta]-glucan on H5NI and H5N2 vaccination using a mouse model", Tropical Medicine and Health, vol. 38, No. 1, Jan. 1, 2010 (Jan. 1, 2010), pp. 23-27.

Ragupathi Get al: "Evaluation of widely consumed botanicals as immunological adjuvants", Vaccine, Elsevier, Amsterdam, NL, vol. 26, No. 37, Sep. 2, 2008 (Sep. 2, 2008), pp. 4860-4865.

Christensen, Dennis, "Vaccine adjuvants: Why and how", Human Vaccines and Immunotherapeutics, 12(10): 2709-2711 (2016); http://dx.doi.org/10.1080/21645515.2016.1219003.

Estevez, et al., Enhancement of the immune response to poorly immunogenic gangliosides after incorporation into very small size proteoliposomes (VSSP), Vaccine 18 (1-2) 190-197 (1999).

Sharmeen, N., et al., Entirely Carbohydrate-Based Vaccines: An Emerging Field for Specific and Selective Immune Responses; Vaccines (Basel); 4(2):19(2016); https://www.ncbi.nlm.nih.gov/pmc/articles/PMC4931636.

* cited by examiner

Figure 3

| Immunization | Death ratio (< 3 mos) | % Survival (>3 mos) |
|---|---|---|
| Naïve control | 37/42 | 11.90% |
| 3F8 iv | 7/9 | 22.20% |
| EL4-irradiated iv | 11/18 | 38.90% |
| EL4-irradiated + 3F8 mix iv | 8/14 | 42.90% |
| EL4-irradiated + 3F8 (2hr) iv | 5/5 | 0% |
| EL4-live + 3F8 mix iv | 9/18 | 50.00% |
| EL4-live + 3F8 (2hr) iv | 22/43 | 48.80% |

* Death ratio = number of mice dead / total number of mice treated

Figure 6

| Prior treatment / immunization | Death ratio (< 3 mos) | % Survival (>3 mos) |
|---|---|---|
| Naïve control | 30/31 | 3.20% |
| EL4-irradiated sc | 13/19 | 31.60% |
| EL4-irradiated + 3F8 + yeast glucan mix sc | 4/5 | 20.00% |
| EL4-live + 3F8 + yeast glucan 4 mg mix sc | 2/5 | 60.00% |
| EL4-live + 3F8 + yeast glucan 2 mg mix sc | 9/22 | 59.10% |
| EL4-live + 3F8 + yeast glucan 1 mg mix sc | 3/5 | 40.00% |
| EL4-live + 3F8 + yeast glucan 0.4 mg mix sc | 17/23 | 26.10% |
| EL4-live + 3F8 + yeast glucan <0.4 mg mix sc | 17/20 | 15.00% |
| EL4-live + 3F8 mix sc | 33/42 | 21.40% |

* Death ratio = number of mice dead / total number of mice treated

Figure 9

|  | Anti-EL4 antibody response | Protection from iv EL4 challenge |
|---|---|---|
| *Wild-type* | | |
| Live vs irradiated EL 4 cells | Yes | Yes |
| 3F8 + EL4 cells vs 3F8 | Yes | Yes |
| *Cell depleted* | | |
| CD4- | No | No |
| Macrophage- | No | No |
| NK- | Yes | No |
| *Knockout mice* | | |
| C3-/- | Yes | Yes |
| CR2-/- | No | NA (susceptible to |
| CR3-/- | Yes | Yes |
| FcRγ-/- | Yes | No |
| FcγRIIB-/- | Yes | NA (resistant to EL4) |
| FcγRIII-/- | Yes | Yes |

Figure 23

| | Anti-tumor Potency (Ramos xenografts in SCID mice day 21 after Rituxan) | | | |
|---|---|---|---|---|
| Botanical Extract | Suppressed tumor growth | Anti-tumor Index | n | p value |
| Control | | | | |
| Astragalus 50% EtOH extract | + | 1.11 | 5 | 0.258 |
| Astragalus 95% EtOH extract | + | 1.12 | 5 | 0.248 |
| Astragalus water extract | + | 1.05 | 5 | 0.422 |
| Coriolus water extract | + | 1.08 | 15 | 0.292 |
| PSK Jiangsu Shenhua | + | 1.07 | 15 | 0.385 |
| PSP Jiangsu Shenhua | + | 1.10 | 15 | 0.261 |
| Tumeric Hydro-ethanol extract | - | 1.06 | 10 | 0.367 |
| β-Glucan, barley | + | 1.18 | 5 | 0.351 |
| β-Glucan, yeast | + | 1.70 | 25 | 0.004 |

Boost 2 sera data

| Ms# | Glucan | FuGM1 KLH | FuGM1-KLH +Glucan | FuGM1 KLH+OPT821 | FuGM1-KLH+OPT821 + Glucan | Pre sera | Grp# |
|---|---|---|---|---|---|---|---|
| | Boost 2 | Boost 2 | Boost 2 | Boost 2 | Boost 2 | pre Grp mean | |
| | | | Binding activity reference to F12 conc. (ug/ml) | | | | |
| M1 | 0.076 | 0.731 | 0.027 | 0.001 | 90.984 | 0.081 | G1 |
| M2 | 0.096 | 19.142 | 0.075 | 14.448 | 13.693 | 0.069 | G2 |
| M3 | 0.104 | 1.544 | 0.665 | 10.695 | 21.583 | 0.084 | G3 |
| M4 | 0.060 | 1.426 | 0.001 | 35.091 | 163.082 | 5.770 | G4 |
| M5 | 0.009 | 1.202 | 0.324 | 44.338 | 1085.596 | 0.324 | G5 |
| Median | 0.076 | 1.426 | 0.075 | 14.448 | 90.984 | 0.084 | Median |
| GeoMean | 0.053 | 2.059 | 0.053 | 2.994 | 86.204 | 0.245 | GeoMean |
| Mean | 0.069 | 4.809 | 0.218 | 20.915 | 274.987 | 1.265 | Mean |

FIG. 30

METHODS OF ENHANCING IMMUNOGENICITY OF POORLY IMMUNOGENIC ANTIGEN-SPECIFIC VACCINES USING ORAL YEAST BETA-GLUCANS

CROSS-REFERENCE TO RELATED APPLICATIONS

This application is a U.S. National Stage Application under 35 U.S.C. § 371 of International Patent Application No. PCT/US2019/028813, filed on Apr. 23, 2019, which claims the benefit of and priority to U.S. provisional Patent Application No. 62/662,176, filed on Apr. 24, 2018, the contents of each of which are incorporated herein by reference in their entireties.

TECHNICAL FIELD

The present technology relates to methods for enhancing the immunogenicity of poorly immunogenic antigen-specific vaccines as well as methods for increasing gut microbiome diversity in a subject in need thereof comprising administering to the subject an effective amount of a beta-glucan extract derived from yeast. Kits for use in practicing the methods are also provided.

BACKGROUND

The following description of the background of the present technology is provided simply as an aid in understanding the present technology and is not admitted to describe or constitute prior art to the present technology.

Adjuvants for human vaccines is a major unmet need (O'Hagan et al., Curr Opin Immunol 47:93-102 (2017)). Adjuvants act via activation of the innate immune system (Coffman et al., Immunity 33:492-503 (2010)) and provide activation signals to modulate the adaptive immune response, thereby priming antigen-specific T helper cells with signature cytokine profiles associated with protection. To improve the immunogenicity of vaccines, co-administration with an adjuvant is required. HIV, tuberculosis, malaria and flu vaccines have not completely realized their full potential because of the insufficient quantity and quality of the induced immune response. Besides infectious diseases, adjuvants for cancer (Saxena & Bhardwaj, Curr Opin Immunol 47:35-43 (2017)) and Alzheimer's disease vaccines (Novak et al., Lancet Neurol 16:123-134 (2017)) are also suboptimal. Pathway specific agonists (e.g. for Toll-like receptors) are precision therapeutics, but their complexity and clinical toxicities could discourage their combinations with other biologics.

Thus, there is an urgent need for safe and effective adjuvants in immune disadvantaged populations such as children, the elderly, and the immunocompromised (Kollmann & Marchant, Trends Immunol 37:523-534 (2016); Mohr & Siegrist, Curr Opin Immunol 41:1-8 (2016); Schaffner et al., Am J Med (2018)).

SUMMARY OF THE PRESENT TECHNOLOGY

In one aspect, the present disclosure provides a method for enhancing the immunogenicity of a poorly immunogenic antigen-specific vaccine in a subject in need thereof comprising: (a) administering to the subject an effective amount of the poorly immunogenic antigen-specific vaccine, wherein the poorly immunogenic antigen-specific vaccine (i) comprises at least one poorly immunogenic antigen that is optionally linked to a carrier, wherein the at least one poorly immunogenic antigen is a peptide, a polypeptide, a nucleic acid, a carbohydrate, or a lipid; and (ii) is not a whole cell tumor vaccine; and (b) administering to the subject an effective amount of a yeast beta-glucan comprising a plurality of β-(1,3) side chains linked to a β-(1,3) backbone via β-(1,6) linkages, and wherein the yeast beta-glucan has a range of average molecular weights from about 6 kDa to about 30 kDa, and wherein the immunogenicity of the poorly immunogenic antigen-specific vaccine in the subject is increased compared to that observed in a control subject that is not treated with the yeast beta-glucan. The subject may be an immunocompromised subject, a pediatric subject, a geriatric subject, or a healthy subject. In certain embodiments, the subject has been exposed to chemoradiotherapy. Additionally or alternatively, in some embodiments, the at least one poorly immunogenic antigen is a peptide, a polypeptide, a nucleic acid, a carbohydrate, or a lipid that is associated with a disease or infection. Examples of such diseases and infections include, but are not limited to neurodegenerative disease, Alzheimer's Disease, melanoma, neuroblastoma, glioma, small cell lung cancer, t-ALL, breast cancer, brain tumors, retinoblastoma, Ewing's sarcoma, osteosarcoma, ovarian cancer, non-Hodgkin's lymphoma, Epstein-Barr related lymphoma, Hodgkin's lymphoma, leukemia, epidermoid carcinoma, prostate cancer, renal cell carcinoma, transitional cell carcinoma, lung cancer, colon cancer, liver cancer, stomach cancer, gastrointestinal cancer, pancreatic cancer, HIV, tuberculosis, malaria, influenza, Ebola, chicken pox, Hepatitis B, HPV, tetanus, pneumococcus, measles, mumps, rubella, influenza, polio, diphtheria, tetanus, pertussis, Rous Sarcoma Virus, rabies, and rotavirus.

Additionally or alternatively, in some embodiments, the structure of the at least one poorly immunogenic antigen is Formula I

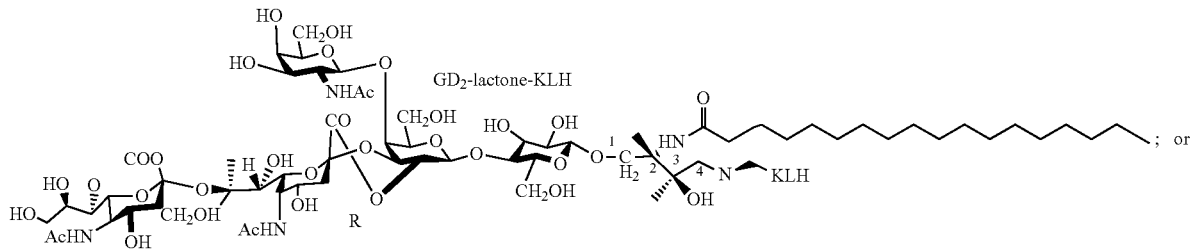

-continued

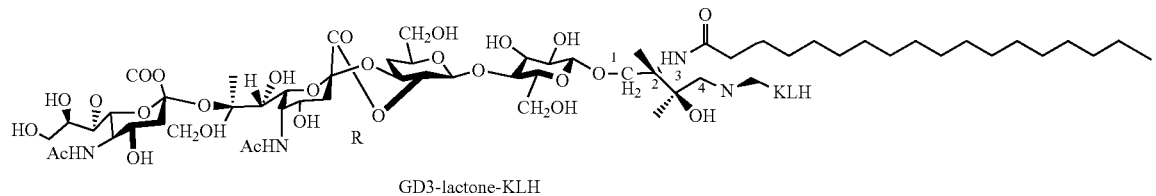

GD3-lactone-KLH

Additionally or alternatively, in some embodiments, the at least one poorly immunogenic antigen is inactivated, partially purified or recombinant hemagglutinin (HA) protein or fucosyl GM1. Examples of the carrier include keyhole limpet hemocyanin, serum globulins, serum albumins, and ovalbumins.

Additionally or alternatively, in some embodiments, the poorly immunogenic antigen-specific vaccine and the yeast beta-glucan are administered separately, sequentially, or simultaneously. In certain embodiments, the poorly immunogenic antigen-specific vaccine is administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments, the yeast beta-glucan is administered intravenously, intramuscularly, intraarterially, intrathecally, intracapsularly, intraorbitally, intradermally, intraperitoneally, transtracheally, subcutaneously, intracerebroventricularly, orally or intranasally. In any of the above embodiments, the yeast beta-glucan is administered daily for 14 days, followed by 14 days of no yeast beta-glucan treatment for a total of 13 cycles.

Additionally or alternatively, in some embodiments, administration of the poorly immunogenic antigen-specific vaccine and the yeast beta-glucan results in about a 1.5-fold, a 2-fold, a 2.5 fold, a 3-fold, a 3.5 fold, a 4-fold, a 4.5 fold, a 5-fold, a 5.5 fold, a 6-fold, a 6.5 fold, a 7-fold, a 7.5 fold, an 8-fold, an 8.5 fold, a 9-fold, a 9.5 fold, or 10-fold increase in therapeutic antibody titer levels in the subject compared to that observed in the subject prior to administration of the poorly immunogenic antigen-specific vaccine and the yeast beta-glucan. In certain embodiments, administration of the poorly immunogenic antigen-specific vaccine and the yeast beta-glucan results in the persistence of therapeutic antibody titer levels in the subject. In any of the above embodiments, administration of the yeast beta-glucan prolongs survival and/or prevents tumor recurrence in the subject.

In another aspect, the present disclosure provides a method for increasing gut microbiome biodiversity in a subject in need thereof comprising administering to the subject an effective amount of a yeast beta-glucan comprising a plurality of β-(1,3) side chains linked to a β-(1,3) backbone via β-(1,6) linkages, and wherein the yeast beta-glucan has a range of average molecular weights from about 6 kDa to about 30 kDa, and wherein administration of the yeast beta-glucan results in an increase in gut microbiome biodiversity compared to that observed in the subject prior to administration of the yeast beta-glucan. The subject may be an immunocompromised subject, a pediatric subject, a geriatric subject, or a healthy subject. In some embodiments, the subject has been exposed to induction chemotherapy and/or exhibits dysbiosis.

Additionally or alternatively, in some embodiments, the subject is diagnosed with or suffers from a disease or infection. Examples of such diseases and infections include, but are not limited to neurodegenerative disease, Alzheimer's Disease, melanoma, neuroblastoma, glioma, small cell lung cancer, t-ALL, breast cancer, brain tumors, retinoblastoma, Ewing's sarcoma, osteosarcoma, ovarian cancer, non-Hodgkin's lymphoma, Epstein-Barr related lymphoma, Hodgkin's lymphoma, leukemia, epidermoid carcinoma, prostate cancer, renal cell carcinoma, transitional cell carcinoma, lung cancer, colon cancer, liver cancer, stomach cancer, gastrointestinal cancer, pancreatic cancer, HIV, tuberculosis, malaria, influenza, Ebola, chicken pox, Hepatitis B, HPV, tetanus, pneumococcus, measles, mumps, rubella, influenza, polio, diphtheria, tetanus, pertussis, Rous Sarcoma Virus, rabies, and rotavirus. Additionally or alternatively, in some embodiments, the yeast beta-glucan is administered intravenously, intramuscularly, intraarterially, intrathecally, intracapsularly, intraorbitally, intradermally, intraperitoneally, transtracheally, subcutaneously, intracerebroventricularly, orally or intranasally.

Also disclosed herein, are kits comprising a solubilized yeast beta-glucan, a poorly immunogenic antigen-specific vaccine, and instructions for use, wherein the solubilized yeast beta-glucan comprises a plurality of β-(1,3) side chains linked to a β-(1,3) backbone via β-(1,6) linkages, and has a range of average molecular weights from about 6 kDa to about 30 kDa. In some embodiments of the kits of the present technology, the poorly immunogenic antigen-specific vaccine comprises at least one poorly immunogenic antigen that is optionally linked to a carrier, wherein the at least one poorly immunogenic antigen is a peptide, a polypeptide, a nucleic acid, a carbohydrate, or a lipid. Additionally or alternatively, in some embodiments of the kits of the present technology, the at least one poorly immunogenic antigen is one or more of GD2 lactone, GD3 lactone, fucosyl GM1, and hemagglutinin (HA) protein. Examples of the carrier include keyhole limpet hemocyanin, serum globulins, serum albumins, and ovalbumins.

Additionally or alternatively, in some embodiments of the kits, the solubilized yeast beta-glucan and/or the poorly immunogenic antigen-specific vaccine is formulated for intravenous, intramuscular, intraarterial, intrathecal, intracapsular, intraorbital, intradermal, intraperitoneal, transtracheal, subcutaneous, intracerebroventricular, oral or intranasal administration.

BRIEF DESCRIPTION OF THE DRAWINGS

FIG. 3 shows a summary of the mice survival data after IV EL4 challenge following intravenous immunization with EL4 tumor cells and 3F8 mAb, as described and shown in FIG. 2.

FIG. 6 shows a summary of the mice survival data after IV EL4 challenge following subcutaneous immunization with EL4 tumor cells and 3F8 mAb and yeast beta-glucan, as described and shown in FIG. 5.

FIG. 9 shows the summary of the anti-EL4 tumor antibody response and tumor protection in CD4 T cell-, macrophage-, or NK cell-depleted mice and CR3-, CR2-, CR3-, FcRγ-, FcγRIIB- or FcγRIII-deficient mice.

FIG. 23 shows the summary of the anti-tumor potency of Rituxan (Rit) in combination with different botanical adjuvants as described and shown in FIG. 22.

DETAILED DESCRIPTION

Figure 1:
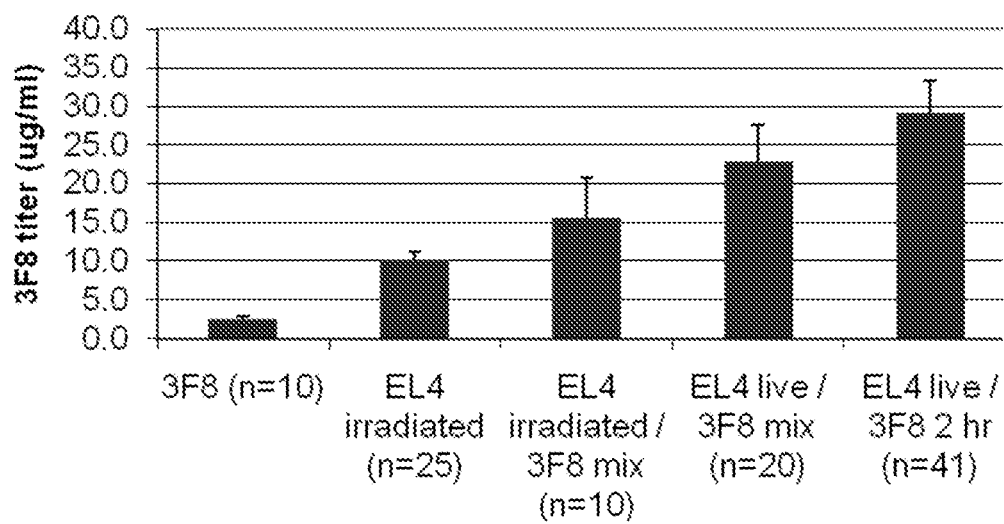
FIG. 1 shows the mouse serum anti-EL4 tumor antibody titers at week 8 after C57BL/6 mice were immunized intravenously with $5 \times 10^4$ irradiated or live EL4 lymphoma tumor cells with 200 μg of the tumor-reactive anti-GD2 monoclonal antibody (mAb) 3F8. Live tumor cells were sometimes pre-mixed with 3F8 and then injected through the tail vein. Alternatively, live tumor cells were injected through the tail vein 2 hours prior to 3F8 administration. Mouse serum anti-EL4 tumor antibody titers were assayed by ELISA using a standard curve generated by 3F8. Data represent mean+standard error. Live tumor cells with 3F8 generated a significant serum anti-tumor antibody response compared to control mice receiving 3F8 only (p<0.01) and a trend of higher serum antibody response was obtained with live tumor cells compared to irradiated tumor cells (p=0.344).

Previous studies have demonstrated that co-administration of antigen-specific vaccines comprising a poorly immunogenic antigen with conventional adjuvants such as QS-21 (OPT-821) have been ineffective in inducing a uniform and robust immune response in human patients (Carvajal et al., J. Clinical Oncology 32 (15): 10520 (2014); Chiun-Sheng Huang et al., J. Clinical Oncology 34 (15): 1003 (2014); Kirkwood et al., J. Clinical Oncology 19 (9): 2370-2380 (2001)).

The present disclosure demonstrates that co-administration of antigen-specific vaccines along with the yeast beta-glucan compositions disclosed herein yielded up to a 10-fold increase in therapeutic antibody titer levels in recipient subjects. The therapeutic antibody titer levels observed using the yeast beta-glucan compositions of the present technology were substantially higher than those observed with the classic saponin adjuvant QS-21. See FIG. 13 and Carvajal et al., J. Clinical Oncology 32 (15): 10520 (2014). Moreover, the concurrent improvement of both anti-GD2 and anti-GD3 antibody titers in patients receiving bivalent GD2/GD3 vaccines demonstrates that no antigenic competition is observed when a mixture of antigens is used with the yeast beta-glucan compositions of the present technology. Further, patients that receive the yeast beta-glucan compositions of the present technology show a greater persistence of therapeutic antibody titer levels compared to that observed in patients that do not receive the yeast beta-glucan compositions. Compare with Krug et al., Clinical Cancer Research 10:6094-6100 (2004); Cappello et al., Cancer Immunol Immunother 48:483-492 (1999); Dickler et al., Clinical Cancer Research 5:2773-2779 (1999); and Ragupathi et al., Clinical Cancer Research 9:5214-5220 (2003).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

An "adjuvant" refers to one or more substances that cause stimulation of the immune system. In this context, an adjuvant is used to enhance an immune response to one or more vaccine antigens. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors. Table 1 provides a summary of adjuvants in clinical trials.

TABLE 1

Adjuvants in clinical development

| | Company | Class | Indications | Stage |
|---|---|---|---|---|
| Montanide | Various | O/W emulsion | Malaria, cancer | Phase III |
| PLG | Novartis | Polymeric microparticles | DNA vaccine (HIV) | Phase I |
| Flagellin | Vaxinnate | Flagellin linked o antigen | Flu | Phase I |
| QS21 | Antigenics | Saponin | Various | Phase I |
| AS01 | GSK | MPL + liposome + QS21 | Malaria, TB | Phase I |
| AS02 | GSK | MPL + W/O emulsion + QS21 | Malaria | Phase I |
| AS15 | GSK | AS01 + CpG | breast cancer | Phase I |
| RC529 | Dynavax | Synthetic MPL + Alum | HBV | Phase II |
| L-BLP25 | Merck | Liposomes + MPL | NSCLC | Phase III |
| ISCOM | CSL, Isconova | Saponins + cholesterol + phospholipids | Various | Phase I |
| IC31 | Intercell | Peptide + oligonucleotide | TB | Phase I |
| CpG | Coley/ Pfizer, Novartis, Idera | Oligonucleotide + Alum, oligonucleotide + MF59, oligonucleotide | HBV, malaria, HVC, cancer | |

TABLE 1-continued

Adjuvants in clinical development

| | Company | Class | Indications | Stage |
|---|---|---|---|---|
| MF59 + MTP-PE | Chiron/ Novartis | Lipidated MDP + O/W emulsion | HIV, Flu | Phase I |
| ISS | Dynavax | Oligonucleotide alum | HBV | Phase II |

As used herein, an "antigen" refers to a molecule to which an antibody can selectively bind. The antigen may be a protein, carbohydrate, nucleic acid, lipid, hapten, or other naturally occurring or synthetic compound. However, some antigens fail to elicit antibody production by themselves. Antigens that are capable of inducing antibody production on their own are referred to as "immunogens."

As used herein, the term "cancer" refers to pathological process that results in the formation and growth of a cancerous or malignant neoplasm, and includes, but is not limited to, neuroblastoma, melanoma, non-Hodgkin's lymphoma, Epstein-Barr related lymphoma, Hodgkin's lymphoma, retinoblastoma, small cell lung cancer, brain tumors, leukemia, epidermoid carcinoma, prostate cancer, renal cell carcinoma, transitional cell carcinoma, breast cancer, ovarian cancer, lung cancer colon cancer, liver cancer, stomach cancer, and other gastrointestinal cancers.

As used herein, a "carrier" is an exogenous protein to which small, non-immunogenic or poorly immunogenic antigens (e.g., haptens) can be conjugated to so as to enhance the immunogenicity of the antigens. Examples of such carriers include keyhole limpet hemocyanin (KLH), serum globulins, serum albumins, ovalbumins, and the like.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of cancer or infection. As used herein, a "therapeutically effective amount" of a composition refers to composition levels in which the physiological effects of a disease or condition are ameliorated or eliminated. A therapeutically effective amount can be given in one or more administrations.

As used herein, the term "hapten" refers to a non-immunogenic or poorly immunogenic molecule that can selectively bind to an antibody, but cannot induce an adaptive immune response on its own. Haptens must be chemically linked to protein carriers to elicit antibody and T cell responses.

As used herein, "higher order conformation" refers to the three-dimensional shape formed by two or more glucan molecules interacting with one another and establishing relatively stable interchain associations through hydrogen bonds.

As used herein, "immune response" refers to the action of one or more of lymphocytes, antigen presenting cells, phagocytic cells, granulocytes, and soluble macromolecules produced by the aforementioned cells or the liver or spleen (including antibodies, cytokines, and complement) that results in selective damage to, destruction of, or elimination from the human body of cancerous cells, metastatic tumor cells, infectious pathogens etc. An immune response may include a cellular response, such as a T-cell response that is an alteration (modulation, e.g., significant enhancement, stimulation, activation, impairment, or inhibition) of cellular, i.e., T-cell function. An immune response may also include humoral (antibody) response.

As used herein, the terms "individual", "patient", or "subject" are used interchangeably and refer to an individual organism, a vertebrate, a mammal, or a human. In certain embodiments, the individual, patient or subject is a human.

As used herein, "induction therapy" refers to the first treatment given for a neoplastic disease and is often part of a standard set of treatments, such as surgery followed by chemotherapy and radiation.

As used herein, the term "overall survival" or "OS" means the observed length of life from the start of treatment to death or the date of last contact.

As used herein, the term "polypeptide," means a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "poorly immunogenic antigen" refers to an antigen that does not elicit a protective or therapeutically effective response in a patient, e.g., an antigen that does not induce an immune response that is sufficient to treat or prevent a disease or condition described herein or one or more signs or symptoms associated with a disease or condition described herein.

As used herein, "prevention" or "preventing" of a disease or medical condition refers to a compound that, in a statistical sample, reduces the occurrence of the disease or medical condition in the treated sample relative to an untreated control sample, or delays the onset of one or more symptoms of the disease or medical condition relative to the untreated control sample.

As used herein, "progression free survival" or "PFS" is the time from treatment to the date of the first confirmed disease progression per RECIST 1.1 criteria.

"RECIST" shall mean an acronym that stands for "Response Evaluation Criteria in Solid Tumors" and is a set of published rules that define when cancer patients improve ("respond"), stay the same ("stable") or worsen ("progression") during treatments. Response as defined by RECIST criteria have been published, for example, at Journal of the National Cancer Institute, Vol. 92, No. 3, Feb. 2, 2000 and RECIST criteria can include other similar published definitions and rule sets. One skilled in the art would understand definitions that go with RECIST criteria, as used herein, such as "Partial Response (PR)," "Complete Response (CR)," "Stable Disease (SD)" and "Progressive Disease (PD)."

As used herein, a "sample" or "biological sample" may be a body fluid or a tissue sample isolated from a subject. In some cases, a biological sample may consist of or comprise whole blood, platelets, red blood cells, white blood cells, plasma, sera, urine, feces, epidermal sample, vaginal sample, skin sample, cheek swab, sperm, amniotic fluid, cultured cells, bone marrow sample, tumor biopsies, aspirate and/or chorionic villi, cultured cells, endothelial cells, synovial fluid, lymphatic fluid, ascites fluid, interstitial or extracellular fluid and the like. The term "sample" may also encompass the fluid in spaces between cells, including gingival crevicular fluid, bone marrow, cerebrospinal fluid (CSF), saliva, mucus, sputum, semen, sweat, urine, or any other bodily fluids. Samples can be obtained from a subject by any means including, but not limited to, venipuncture, excretion, ejaculation, massage, biopsy, needle aspirate, lavage, scraping, surgical incision, or intervention or other means known in the art. A blood sample can be whole blood or any fraction thereof, including blood cells (red blood cells, white blood cells or leucocytes, and platelets), serum and plasma.

As used herein, the term "separate" therapeutic use refers to an administration of at least two active ingredients at the same time or at substantially the same time by different routes As used herein, the term "sequential" therapeutic use refers to administration of at least two active ingredients at different times. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, "survival" refers to the subject remaining alive, and includes overall survival as well as progression free survival.

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

The term "vaccine" as used herein is a preparation used to enhance protective immunity against cancer, or infectious agents such as viruses, fungi, bacteria and other pathogens. A vaccine may be useful as a prophylactic agent or a therapeutic agent. Vaccines contain cells or antigens which, when administered to the body, induce an immune response with the production of antibodies and immune lymphocytes (T-cells and B-cells).

"Whole cell tumor vaccines", also referred to as "whole tumor vaccines" comprise tumor cells which may be autologous or allogeneic for the patient and comprise cancer antigens which can stimulate the body's immune system. Unlike the administration of an antigen-specific vaccine, a whole cell tumor vaccine exposes a large number of cancer specific (unique or up-regulated) antigens to the patient's immune system. The whole cell tumor vaccine may comprise intact cells or a cell lysate. The use of such a lysate or intact cell preparation means that the vaccine will comprise in excess of 10 antigens, typically in excess of 30 antigens. Whole cell tumor vaccines may comprise tumor cells that have been modified in vitro, e.g., irradiated and dead tumor cells or live tumor cells.

Yeast Beta-Glucans of the Present Technology

Beta-glucans are polymers containing a backbone of beta-1,3-linked and beta-1,4-D-glucose molecules with 1,6-linked side-chains. The frequency of these side-chains regulates secondary structures and biochemical properties. Beta-glucans are found in many foods, such as mushrooms, oats, rice, barley, seaweed, baker's yeast and fungi. Glucan-containing extracts include Lentinan (from Shiitake mushroom), PSK (from *Coriolus versicolor*, laminarin (from seaweed), Schizophyllan, Betafectin and Maitake d-fraction. Beta-1,3-glucan is the component responsible for the majority of biological activities of zymosan, a commonly used leukocyte stimulant derived from the cell wall of Bakers' yeast (*Saccharomyces cerevisiae*).

Depending upon the source and method of isolation, beta-glucans have various degrees of branching and of linkages in the side chains. The frequency and hinge-structure of side chains determine its immunomodulatory effect. Beta-glucans of fungal and yeast origin are normally insoluble in water, but can be made soluble either by acid hydrolysis or derivatization by introducing charged groups like phosphate, sulfate, amine, carboxymethyl and so forth to the molecule (Seljelid R, Biosci. Rep. 6:845-851 (1986); Williams et al., Immunopharmacology 22:139-156 (1991)).

Figure 10:
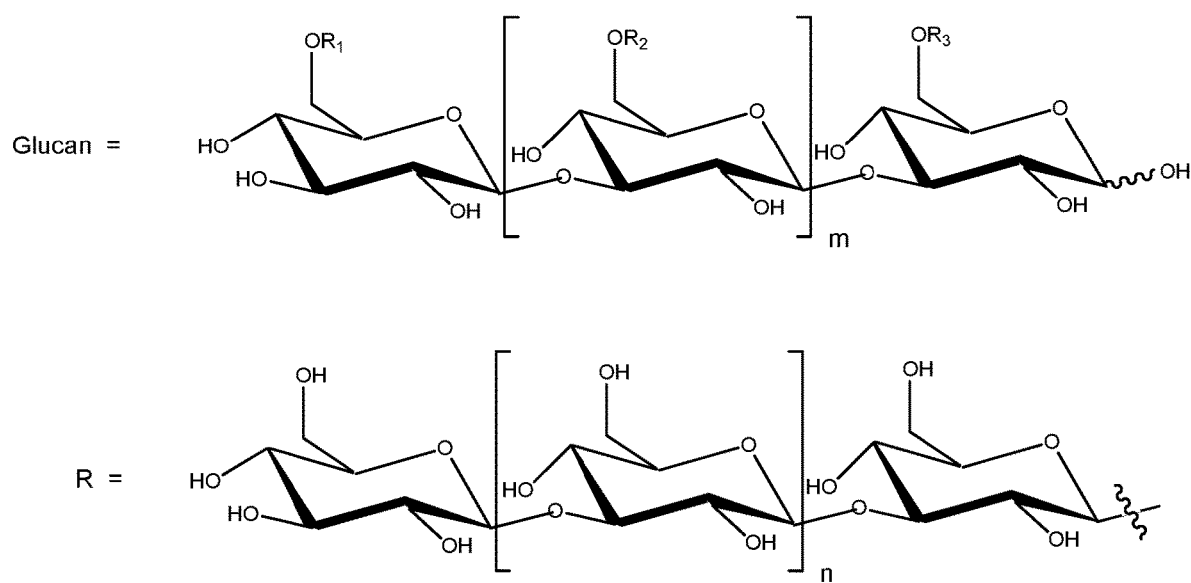
FIG. 10 shows the generic structure of a yeast beta-glucan comprising a plurality of β-(1,3) side chains linked to a β-(1,3) backbone via β-(1,6) linkages. $R_1$, $R_2$ and $R_3$ are independently H or R (formula also shown in FIG. 10), n is an integer from 0 to about 50, m is an integer from about 35 to about 2000, each of the m glucose units may have different $R_2$ and n, and there is at least one R group on the glucan.

The yeast beta-glucans of the present technology comprises a plurality of β-(1,3) side chains linked to a β-(1,3) backbone via β-(1,6) linkages, and has a range of average molecular weights from about 6 kDa to about 30 kDa, from about 6 kDa to about 25 kDa, or from about 16 kDa to about 17 kDa (Biotec Pharamacon ASA, Tromsø, Norway). FIG. 10 shows the generic structure of the yeast beta-glucans of the present technology. An exemplar molecular structure of the yeast beta-glucans of the present technology is provided below (n is an integer from 0 to about 50, m is an integer from about 35 to about 2000):

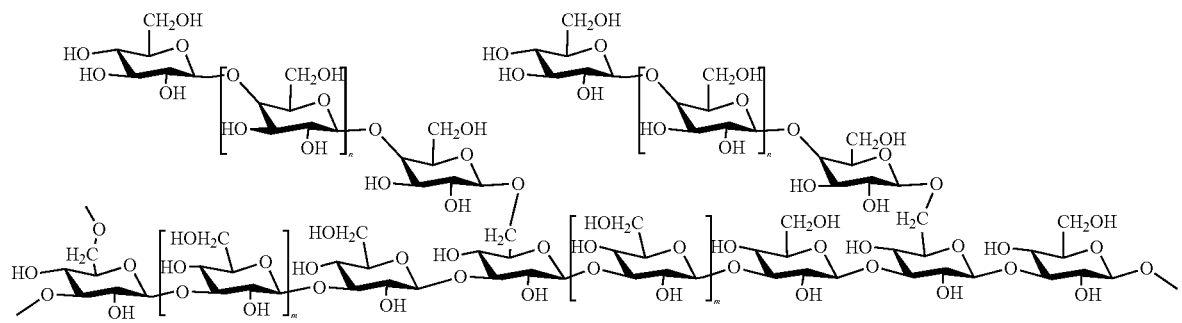

Figure 11:
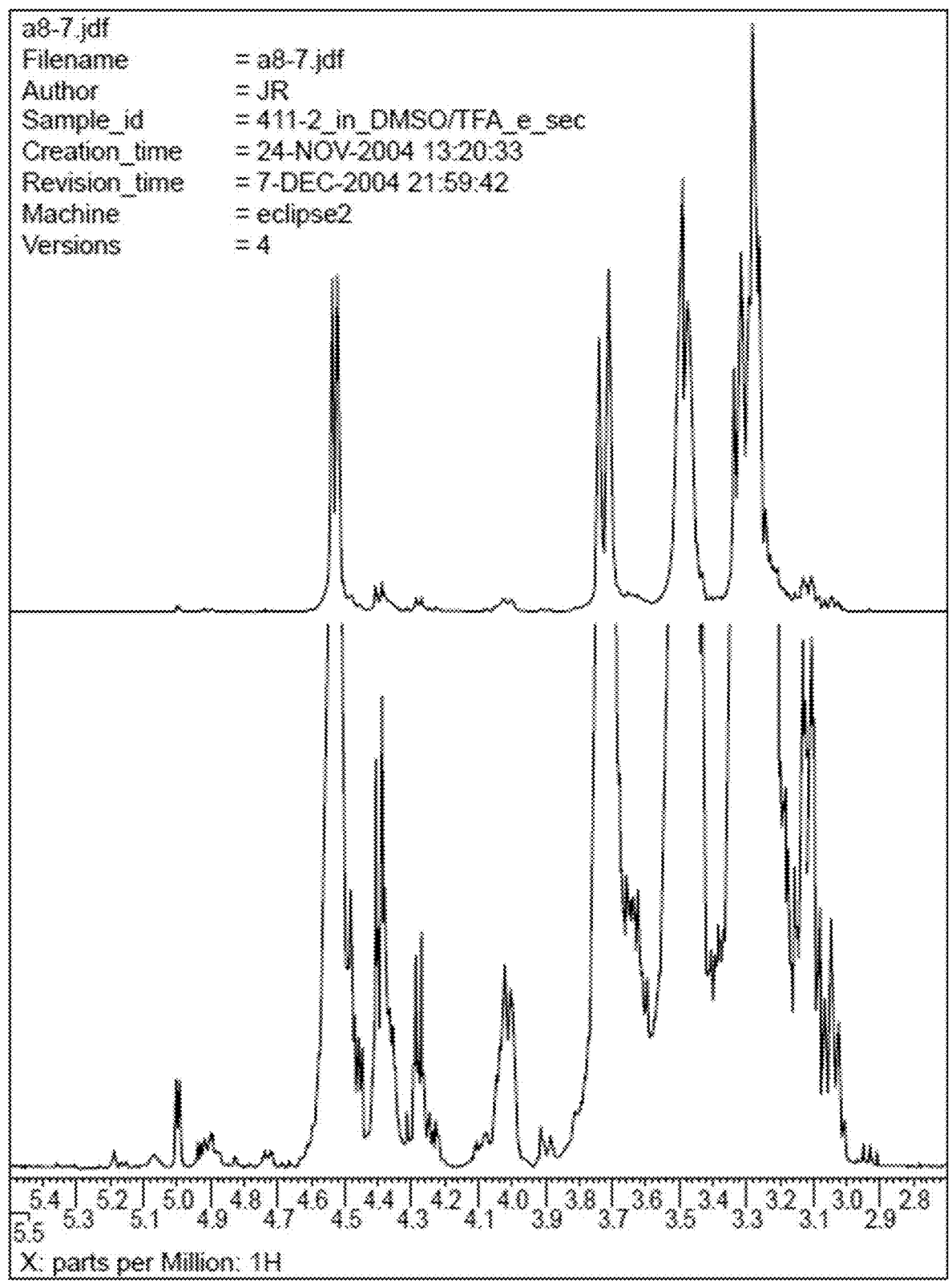
FIG. 11 shows the 1H NMR spectrum of a typical yeast soluble beta-glucan (SBG) sample (Biotec Pharmacon ASA, Tromsø, Norway). An SBG sample was dissolved in DMSO-d6 at a concentration of approximately 20 mg/ml and with a few drops of TFA-d added. The spectrum (cut-out from 2.7 to 5.5 ppm) was collected over 2 hours on a JEOL ECX 400 NMR spectrometer at 80° C. Chemical shifts were referenced to residual proton resonance from the DMSO-d6 at 2.5 ppm, and the spectrum was baseline corrected.
Figure 12:
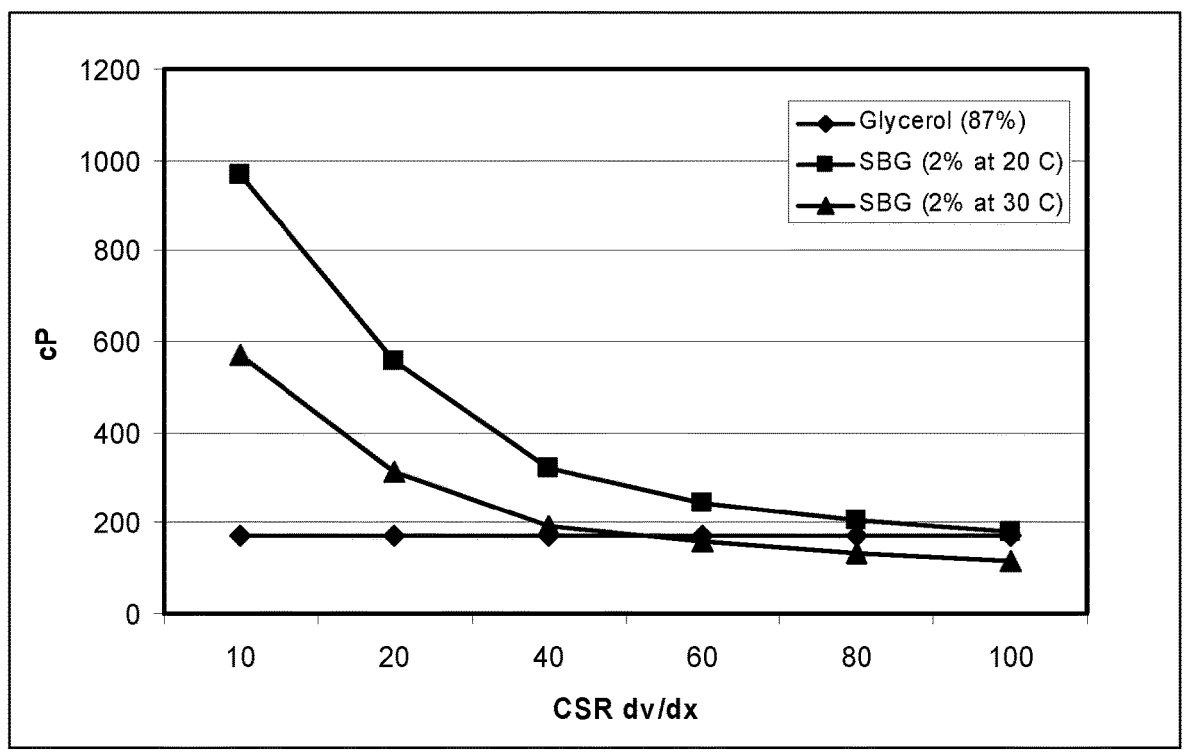
FIG. 12 shows the viscosity profile of SBG. Profiles for a 2% solution of SBG at 20° C. or 30° C. at different shear rates are shown. Glycerol (87% solution) was used as a reference solution.

The beta-glucan molecules form a higher order conformation, resulting in gelling and high viscosity profile. The NMR profile and viscosity profile of the yeast beta-glucans of the present technology are shown in FIG. 11 and FIG. 12, respectively.

The yeast beta-glucans of the present technology are treated with a hydrolyzing agent like an acid or enzyme to significantly reduce or eliminate (1,6) linkages within the glucan branches (a single (1,6) link is required to form the branch). In some embodiments, less than 10%, less than 5%, less than 3% or less than 2% of the glycosidic bonds in the beta-glucan molecule will be (1,6) linkages. These products can be particulate, semi-soluble, soluble or a gel. In certain embodiments, production of solubilized yeast beta-glucans include the addition of formic acid to the extracted yeast beta-glucans to a final concentration of 75% w/v and heating the suspension to facilitate formolysis. An example of a soluble hydrolyzed yeast beta-glucan of the present technology is Soluble Beta Glucan (Biotec Pharmacon ASA, Tromsø, Norway). Soluble Beta Glucan is an underivatized (in terms of chemical modifying groups) aqueous soluble β-1,3/1,6-glucan, characterized by NMR and chemical analysis as containing a linear β-1,3-glucan backbone having side chains of β-1,3-linked D-glucose units wherein the side chains are attached to the backbone via β-1,6-linkages, wherein the number of B-1,6 moieties in the side chains (not including at the backbone/side chain branch point) is considerably reduced as compared to the structure of said glucan in the yeast cell wall. Soluble Beta Glucan presents durable interchain associations as demonstrated by its high viscosity profile and gelling behavior (FIG. 12). A non-limiting example of such a composition is:

| Ingredient | Range | Typical Value |
|---|---|---|
| 1,3/1,6-beta-D-glucan | 18-22 g/kg | 20 g/kg |
| Proteins | 1 g/kg (max) | <1 g/kg |
| Ash | 1 g/kg (max) | <1 g/kg |
| Water | 977-983 g/kg | 980 g/kg |

Products having the desired structural features and showing a higher order conformation like Solubilized Beta Glucan may be administered orally, intraperitoneally, subcutaneously, intra-muscularly or intravenously. Functional dose range of the glucans can be readily determined by one of ordinary skills in the art. For example, when administered orally the functional dose range would be in the area of 1-500 mg/kg/day, 10-200 mg/kg/day, or 20-80 mg/kg/day. When administered parenterally, the functional dose range may be 0.1-10 mg/kg/day.

In the present technology, a yeast beta-1,3-glucan is used in combination with a poorly immunogenic antigen-specific vaccine. In certain embodiments, the yeast beta-1,3-glucan is administered in the amount of 0.1-4 mg. The above mentioned pharmaceutical compositions may contain pharmaceutically acceptable carriers and other ingredients known to enhance and facilitate drug administration. The relative amounts of the active ingredient, the pharmaceutically acceptable carrier, and any additional ingredients in a pharmaceutical composition of the present technology will vary, depending upon the identity, size, and condition of the subject treated. Such a pharmaceutical composition may comprise the active ingredient alone, in a form suitable for administration to a subject, or the pharmaceutical composition may comprise the active ingredient and one or more pharmaceutically acceptable carriers, one or more additional ingredients, or any combination thereof. The active ingredient may be present in the pharmaceutical composition in forms which are generally well known in the art.

Typically, dosages of the yeast beta-glucans of the present technology administered to a subject, will vary depending upon any number of factors, including but not limited to, the type of subject and type of cancer and disease state being treated, the age of the subject, the route of administration and the relative therapeutic index. The route(s) of administration will be readily apparent to the skilled artisan and will depend upon any number of factors including the type and severity of the disease being treated, the gender and age of the patient being treated, and the like.

Formulations suitable for oral administration of the yeast beta-glucans include, but are not limited to, an aqueous or oily suspension, an aqueous or oily solution, an emulsion or a particulate formulation. Such formulations can be administered by any means including, but not limited to, soft gelatin capsules.

Liquid formulations of the yeast beta-glucans disclosed herein that are suitable for oral administration may be prepared, packaged, and sold either in liquid form or in the form of a dry product intended for reconstitution with water or other suitable vehicle prior to use. Administration can be by a variety of different routes including intravenous, subcutaneous, intranasal, buccal, transdermal and intrapulmonary. One of ordinary skill in the art would be able to determine the desirable routes of administration, and the kinds of formulations suitable for a particular route of administration.

In general, the yeast beta-glucan can be administered to a subject as frequently as several times daily, or it may be administered less frequently, such as once a day. The poorly immunogenic antigen-specific vaccine treatment will for instance depend upon the type of antigen, the type of cancer, the severity of the cancer, and the condition of each patient. The yeast beta-glucan treatment is closely interrelated with the poorly immunogenic antigen-specific vaccine treatment regimen, and could be prior to, concurrent with, or after the administration of the poorly immunogenic antigen-specific vaccine. The frequency of the yeast beta-glucan and poorly immunogenic antigen-specific vaccine dose will be readily apparent to the skilled artisan and will depend upon any number of factors, such as, but not limited to, the extent and severity of the disease being treated, and the type and age of the patients.

Methods of the Present Technology

In one aspect, the present disclosure provides a method for enhancing the immunogenicity of a poorly immunogenic antigen-specific vaccine in a subject in need thereof comprising: (a) administering to the subject an effective amount of the poorly immunogenic antigen-specific vaccine, wherein the poorly immunogenic antigen-specific vaccine (i) comprises at least one poorly immunogenic antigen that is optionally linked to a carrier, wherein the at least one poorly immunogenic antigen is a peptide, a polypeptide, a nucleic acid, a carbohydrate, or a lipid; and (ii) is not a whole cell tumor vaccine; and (b) administering to the subject an effective amount of a yeast beta-glucan comprising a plurality of β-(1,3) side chains linked to a β-(1,3) backbone via β-(1,6) linkages, and wherein the yeast beta-glucan has a range of average molecular weights from about 6 kDa to about 30 kDa, and wherein the immunogenicity of the poorly immunogenic antigen-specific vaccine in the subject is increased compared to that observed in a control subject that is not treated with the yeast beta-glucan. The subject may be an immunocompromised subject, a pediatric subject, a geriatric subject, or a healthy subject. In certain embodiments, the subject has been exposed to chemoradiotherapy. Additionally or alternatively, in some embodiments, the at least one poorly immunogenic antigen is a peptide, a polypeptide, a nucleic acid, a carbohydrate, or a lipid that is associated with a disease or infection. Examples of such diseases and infections include, but are not limited to neurodegenerative disease, Alzheimer's Disease, melanoma, neuroblastoma, glioma, small cell lung cancer, t-ALL, breast cancer, brain tumors, retinoblastoma, Ewing's sarcoma, osteosarcoma, ovarian cancer, non-Hodgkin's lymphoma, Epstein-Barr related lymphoma, Hodgkin's lymphoma, leukemia, epidermoid carcinoma, prostate cancer, renal cell carcinoma, transitional cell carcinoma, lung cancer, colon cancer, liver cancer, stomach cancer, gastrointestinal cancer, pancreatic cancer, HIV, tuberculosis, malaria, influenza, Ebola, chicken pox, Hepatitis B, HPV, tetanus, pneumococcus, measles, mumps, rubella, influenza, polio, diphtheria, tetanus, pertussis, Rous Sarcoma Virus, rabies, and rotavirus.

Additionally or alternatively, in some embodiments, the structure of the poorly immunogenic antigen is

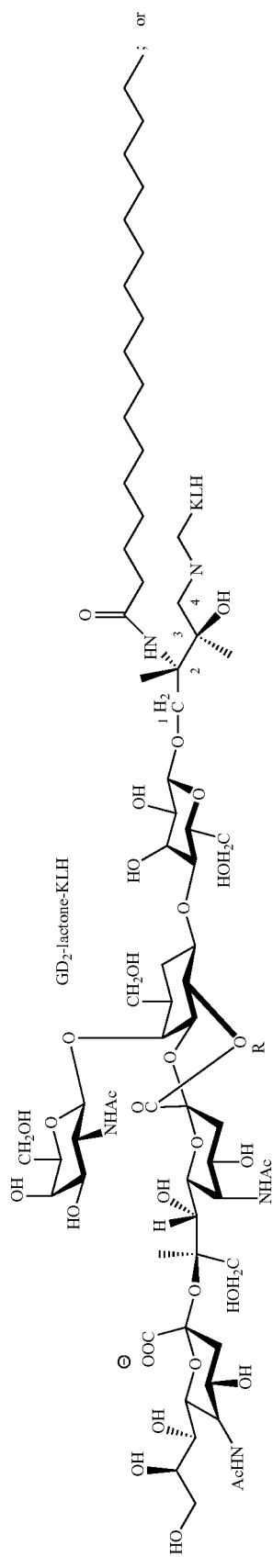
Formula I
GD2-lactone-KLH
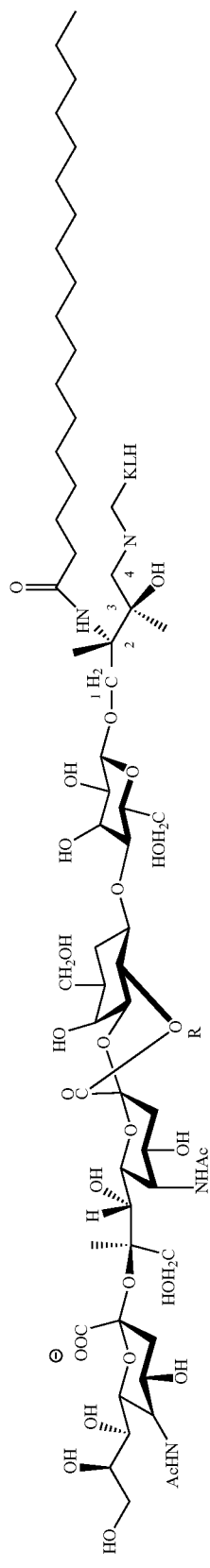
Formula II
GD3-Lactone-KLH

Additionally or alternatively, in some embodiments, the at least one poorly immunogenic antigen is inactivated, partially purified or recombinant hemagglutinin (HA) protein or fucosyl GM1. Examples of the carrier include keyhole limpet hemocyanin, serum globulins, serum albumins, and ovalbumins.

Additionally or alternatively, in some embodiments, the poorly immunogenic antigen-specific vaccine and the yeast beta-glucan are administered separately, simultaneously or sequentially. In certain embodiments, the poorly immunogenic antigen-specific vaccine is administered intravenously, intramuscularly, intraarterially, intrathecally, intracapsularly, intraorbitally, intradermally, intraperitoneally, transtracheally, subcutaneously, intracerebroventricularly, orally or intranasally. In some embodiments, the yeast beta-glucan is administered intravenously, intramuscularly, intraarterially, intrathecally, intracapsularly, intraorbitally, intradermally, intraperitoneally, transtracheally, subcutaneously, intracerebroventricularly, orally or intranasally.

Additionally or alternatively, in some embodiments, administration of the poorly immunogenic antigen-specific vaccine and the yeast beta-glucan results in about a 1.5-fold, a 2-fold, a 2.5 fold, a 3-fold, a 3.5 fold, a 4-fold, a 4.5 fold, a 5-fold, a 5.5 fold, a 6-fold, a 6.5 fold, a 7-fold, a 7.5 fold, an 8-fold, an 8.5 fold, a 9-fold, a 9.5 fold, or 10-fold increase in therapeutic antibody titer levels (e.g., but not limited to anti-GD2 or anti-GD3) in the subject compared to that observed in the subject prior to administration of the poorly immunogenic antigen-specific vaccine and the yeast beta-glucan. In certain embodiments, administration of the poorly immunogenic antigen-specific vaccine and the yeast beta-glucan results in the persistence of therapeutic antibody titer levels (e.g., but not limited to anti-GD2 or anti-GD3) in the subject. In any of the above embodiments, administration of the yeast beta-glucan prolongs survival and/or prevents tumor recurrence in the subject.

In another aspect, the present disclosure provides a method for increasing gut microbiome biodiversity in a subject in need thereof comprising administering to the subject an effective amount of a yeast beta-glucan comprising a plurality of β-(1,3) side chains linked to a β-(1,3) backbone via β-(1,6) linkages, and wherein the yeast beta-glucan has a range of average molecular weights from about 6 kDa to about 30 kDa, and wherein administration of the yeast beta-glucan results in an increase in gut microbiome biodiversity compared to that observed in the subject prior to administration of the yeast beta-glucan. The subject may be an immunocompromised subject, a pediatric subject, a geriatric subject, or a healthy subject. In some embodiments, the subject has been exposed to induction chemotherapy and/or exhibits dysbiosis. In any of the above embodiments, administration of the yeast beta-glucan results in at least a 2%, at least a 3%, at least a 4%, at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least a 70%, at least a 75%, at least a 80%, at least a 85%, at least a 90%, or least a 95% increase in gut microbiome biodiversity compared to that observed in the subject prior to administration of the yeast beta-glucan.

Additionally or alternatively, in some embodiments, the subject is diagnosed with or suffers from a disease or infection. Examples of such diseases and infections include, but are not limited to neurodegenerative disease, Alzheimer's Disease, melanoma, neuroblastoma, glioma, small cell lung cancer, t-ALL, breast cancer, brain tumors, retinoblastoma, Ewing's sarcoma, osteosarcoma, ovarian cancer, non-Hodgkin's lymphoma, Epstein-Barr related lymphoma, Hodgkin's lymphoma, leukemia, epidermoid carcinoma, prostate cancer, renal cell carcinoma, transitional cell carcinoma, lung cancer, colon cancer, liver cancer, stomach cancer, gastrointestinal cancer, pancreatic cancer, HIV, tuberculosis, malaria, influenza, Ebola, chicken pox, Hepatitis B, HPV, tetanus, pneumococcus, measles, mumps, rubella, influenza, polio, diphtheria, tetanus, pertussis, Rous Sarcoma Virus, rabies, and rotavirus. Additionally or alternatively, in some embodiments, wherein the yeast beta-glucan is administered intravenously, intramuscularly, intraarterially, intrathecally, intracapsularly, intraorbitally, intradermally, intraperitoneally, transtracheally, subcutaneously, intracerebroventricularly, orally or intranasally.

In some embodiments of the methods disclosed herein, the yeast beta-glucan is administered one, two, three, four, or five times per day. In some embodiments, the yeast beta-glucan is administered more than five times per day. Additionally or alternatively, in some embodiments, the yeast beta-glucan is administered every day, every other day, every third day, every fourth day, every fifth day, or every sixth day. In some embodiments, the yeast beta-glucan is administered weekly, bi-weekly, tri-weekly, or monthly. In some embodiments, the yeast beta-glucan is administered for a period of one, two, three, four, or five weeks. In some embodiments, the yeast beta-glucan is administered for six weeks or more. In some embodiments, the yeast beta-glucan is administered for twelve weeks or more. In some embodiments, the yeast beta-glucan is administered for a period of less than one year. In some embodiments, the yeast beta-glucan is administered for a period of more than one year. In some embodiments, the yeast beta-glucan is administered throughout the subject's life.

In some embodiments of the methods of the present technology, the yeast beta-glucan is administered daily for 1 week or more. In some embodiments of the methods of the present technology, the yeast beta-glucan is administered daily for 2 weeks or more. In some embodiments of the methods of the present technology, the yeast beta-glucan is administered daily for 3 weeks or more. In some embodiments of the methods of the present technology, the yeast beta-glucan is administered daily for 4 weeks or more. In some embodiments of the methods of the present technology, the yeast beta-glucan is administered daily for 6 weeks or more. In some embodiments of the methods of the present technology, the yeast beta-glucan is administered daily for 12 weeks or more. In some embodiments, the yeast beta-glucan is administered throughout the subject's life. In certain embodiments, the yeast beta-glucan is administered daily for one or more days (1-14 days), followed by one or more days (1-14 days) of no yeast beta-glucan treatment for a total of 1, 2, 3, 4, 5, 6, 7, 8, 9, 10, 11, 12, 13, 14, or 15 or more cycles.

Kits

The present disclosure provides kits comprising a solubilized yeast beta-glucan, a poorly immunogenic antigen-specific vaccine, and instructions for use, wherein the solubilized yeast beta-glucan comprises a plurality of β-(1,3) side chains linked to a β-(1,3) backbone via β-(1,6) linkages, and has a range of average molecular weights from about 6 kDa to about 30 kDa. In some embodiments of the kits of the present technology, the poorly immunogenic antigen-specific vaccine comprises at least one poorly immunogenic antigen that is optionally linked to a carrier, wherein the at least one poorly immunogenic antigen is a peptide, a polypeptide, a nucleic acid, a carbohydrate, or a lipid. The at least one poorly immunogenic antigen is a peptide, a polypeptide, a nucleic acid, a carbohydrate, or a lipid that is associated with any disease or infection, including but not limited to those disclosed herein.

Additionally or alternatively, in some embodiments of the kits of the present technology, the at least one poorly immunogenic antigen is one or more of GD2 lactone, GD3 lactone, fucosyl GM1, and hemagglutinin (HA) protein (e.g., inactivated, partially purified or recombinant hemagglutinin). Examples of the carrier include keyhole limpet hemocyanin, serum globulins, serum albumins, and ovalbumins.

Additionally or alternatively, in some embodiments of the kits, the solubilized yeast beta-glucan and/or the poorly immunogenic antigen-specific vaccine is formulated for intravenous, intramuscular, intraarterial, intrathecal, intracapsular, intraorbital, intradermal, intraperitoneal, transtracheal, subcutaneous, intracerebroventricular, oral or intranasal administration.

Optionally, the above described components of the kits of the present technology are packed in suitable containers and labeled for enhancing the immunogenicity of a poorly immunogenic antigen-specific vaccine in a subject. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, etc. The kits may optionally include instructions customarily included in commercial packages of therapeutic products, that contain information about, for example, the indications, usage, dosage, manufacture, administration, contraindications and/or warnings concerning the use of such therapeutic products.

The kits may also include additional agents that are useful for detecting the therapeutic antibody titer levels in a biological sample including, but not limited to, e.g., serum, plasma, lymph, cystic fluid, urine, stool, cerebrospinal fluid, ascitic fluid or blood and including biopsy samples of body tissue. For example, the kit may comprise: one or more poorly immunogenic antigens (e.g., but not limited to GD2 or GD3) capable of binding to the induced antibodies present in the biological sample, a means for determining the amount of the induced antibodies present in the biological sample, and a means for comparing the amount of the immunoreactive induced antibodies in the biological sample with a standard. The one or more poorly immunogenic antigens may be labeled. The kit components, (e.g., reagents) can be packaged in a suitable container. The kit can further comprise instructions for using the kit to detect the immunoreactive induced antibodies.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of induced antibodies in vitro or in vivo, or for enhancing the immunogenicity of a poorly immunogenic antigen-specific vaccine in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative yeast beta-glucan compositions of the present technology. The following Examples demonstrate the characterization of the efficacy of the beta-glucan compositions of the present technology in vaccines.

Example 1: Adjuvant Effect of Subcutaneous Yeast Beta-Glucan in Whole Tumor Vaccine The combination of tumor cell and anti-tumor mAb was tested as a whole cell tumor vaccine. The model vaccine used in the current study is the combination of a GD2 (+) tumor (EL4) and the anti-GD2 IgG3 antibody 3F8.

Yeast beta-glucan. The yeast beta-glucan used in the present Examples has an average molecular weight of ~16,000 to ~17,000 Daltons, with a range of average molecular weights from ~6,000 to ~30,000 Daltons (FIG. 10). 1H NMR spectrum of a typical SBG sample (Biotec Pharamacon ASA, Tromsø, Norway) is shown in FIG. 11. An SBG sample was dissolved in DMSO-d6 at a concentration of approximately 20 mg/ml and with a few drops of TFA-d added. The spectrum (cut-out from 2.7 to 5.5 ppm) was collected over 2 hours on a JEOL ECX 400 NMR spectrometer at 80° C. Chemical shifts were referenced to residual proton resonance from the DMSO-d6 at 2.5 ppm, and the spectrum was baseline corrected. The viscosity profiles of a 2% solution of SBG at 20° C. or 30° C. at different shear rates are shown in FIG. 12. Glycerol (87% solution) was used as a reference solution.

Figure 2:
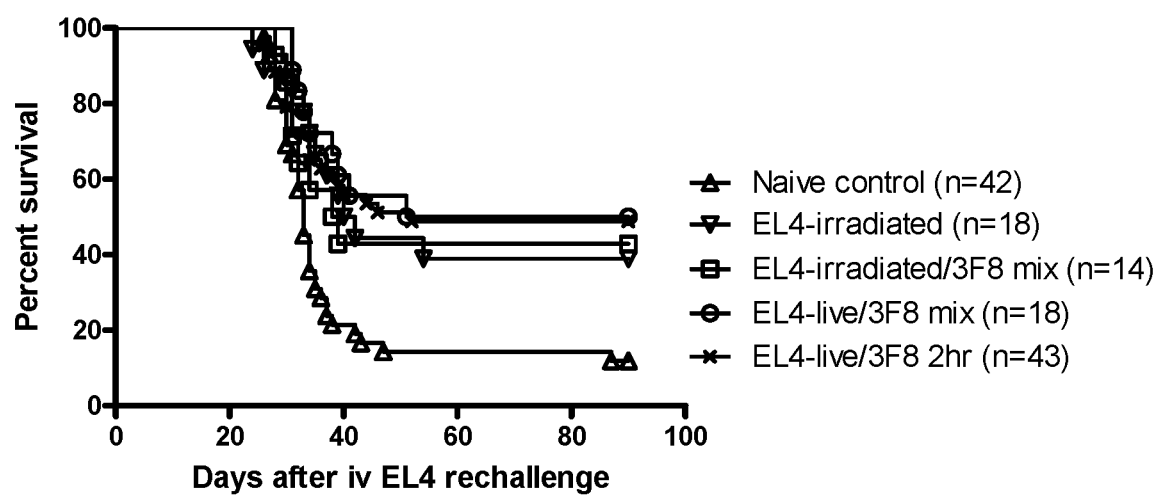
FIG. 2 shows the survival curves of C57BL/6 mice rechallenged with $5 \times 10^4$ EL4 cells (administered intravenously) after intravenous immunization with $5 \times 10^4$ irradiated or live EL4 lymphoma tumor cells with 200 µg tumor-reactive 3F8 mAb. During vaccination, live tumor cells were mixed with the antibody or given 2 hours prior to antibody administration by injection through the tail vein. Mice that received live tumor cells together with 3F8 survived significantly longer than control mice upon tumor intravenous (IV) rechallenge (p<0.05), and were comparable to mice that received irradiated tumor cells or irradiated tumor cells plus 3F8.

Intravenous (IV) EL4 tumor+IV 3F8 MAb. C57BL/6 mice were intravenously immunized through the tail vein with $5 \times 10^4$ live EL4 lymphoma tumor cells in the presence of 200 μg tumor-reactive 3F8 mAb. 3F8 was either (a) directly mixed with tumor cells prior to immunization or (b) given 2 hours after the mice were immunized with the tumor cells to mimic a treatment setting. Irradiated tumor cells were included as a comparison. Mouse serum anti-EL4 tumor antibody titers were assayed by ELISA on EL4 cell plates. Animals that received live tumor cells mixed with 3F8 or live tumor cells treated with 3F8 in 2 hours generated a significant serum anti-tumor antibody response compared with control mice receiving 3F8 only (p<0.01) and a trend of higher serum antibody response was obtained with live tumor cells compared to irradiated tumor cells (p=0.344, FIG. 1). Mice that received live tumor cells together with 3F8 (either direct mixture or 2 hours after tumor cell injection) survived significantly longer than control mice upon tumor IV rechallenge (p<0.05), and were comparable to mice that received irradiated tumor cells or irradiated tumor cells plus 3F8 (FIG. 2 and FIG. 3).

Figure 4:
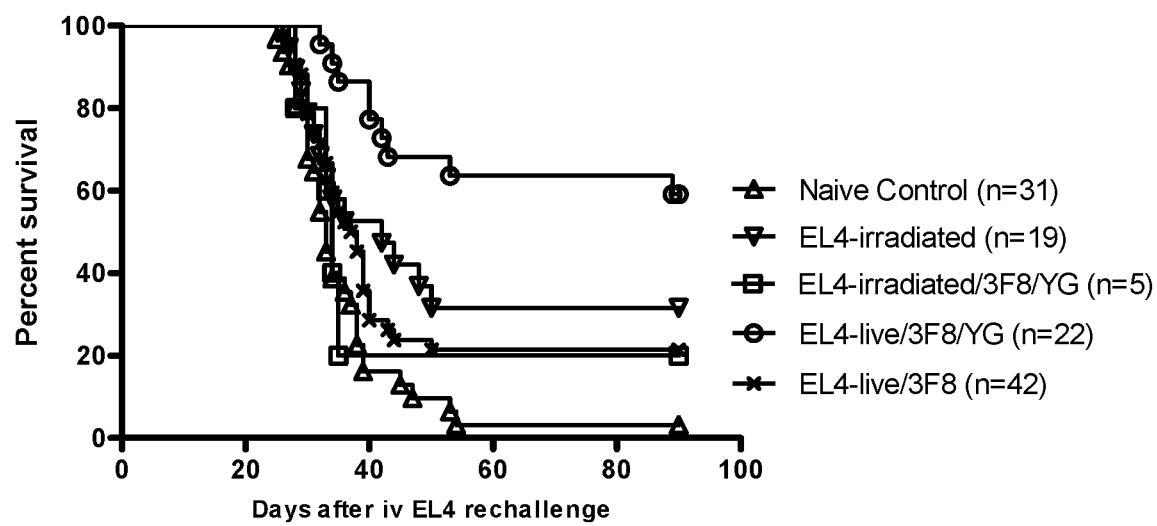
FIG. 4 shows the survival curves of C57BL/6 mice rechallenged with $5 \times 10^4$ EL4 cells IV after subcutaneous immunization with live or irradiated EL4 lymphoma tumor cells ($5 \times 10^5$) in the presence of tumor-reactive mAb 3F8 (50 µg) plus yeast beta-glucan (YG, 2 mg). Mice that received live EL4 and 3F8 survived longer than the naïve control (p<0.05) and mice that received live EL4 and 3F8 plus yeast beta-glucan survived longer than either live EL4 plus 3F8 (p<0.001) or irradiated EL4 (p<0.05).
Figure 5:
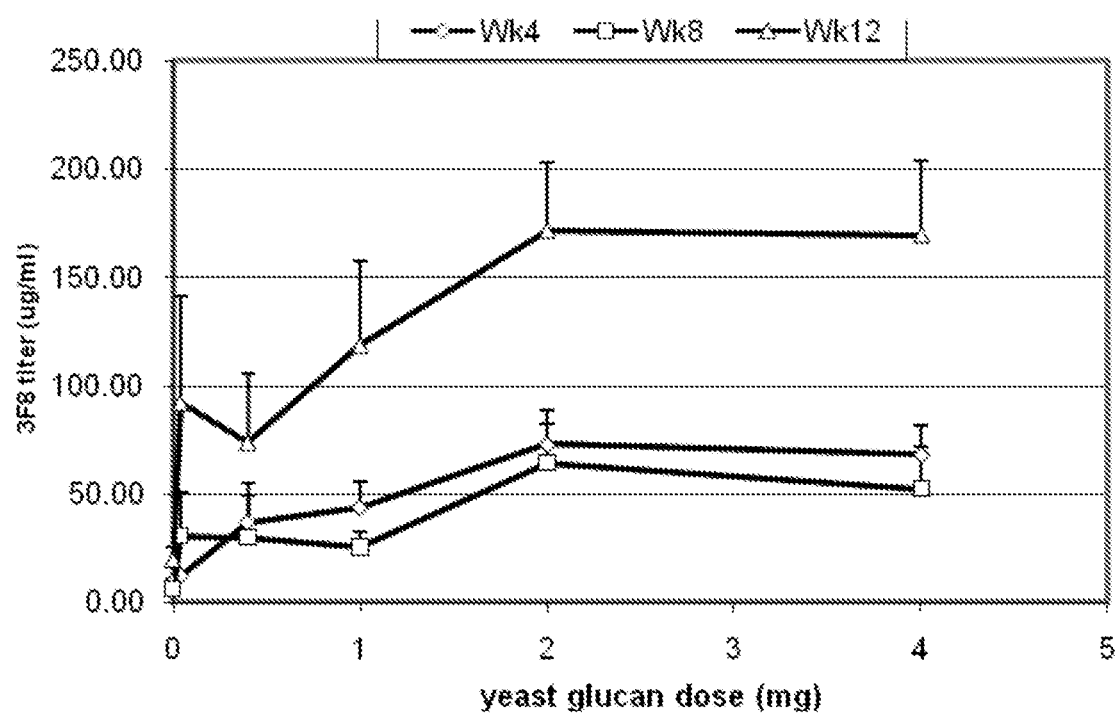
FIG. 5 shows mouse serum anti-EL4 tumor antibody titers at weeks 4, 8 and 12 after C57BL/6 mice were subcutaneously immunized with live EL4 lymphoma tumor cells ($5 \times 10^5$) in the presence of tumor-reactive mAb 3F8 (50 µg) plus yeast beta-glucan (0.1-4 mg). Mouse serum anti-EL4 tumor antibody titers were assayed by ELISA using a standard curve generated by 3F8. Data represent mean+ standard error for 5 mice. Antibody titer against EL4 tumor cells correlated with the dose of yeast glucan.

Subcutaneous (sc) EL4 tumor+sc 3F8 MAb+sc yeast beta-glucan. C57BL/6 mice were immunized subcutaneously with live EL4 lymphoma tumor cells ($5 \times 10^5$) in the presence of tumor-reactive 3F8 (50 µg) plus yeast beta-glucan (0.1-4 mg) (Biotec Pharamacon ASA, Tromsø, Norway). Mouse serum anti-EL4 antibody titers were assayed by ELISA. Like the IV vaccine experiments described above, live tumor cells mixed with 3F8 generated a significantly higher anti-tumor antibody response compared with control mice receiving 3F8 Ab only (p<0.01). Mice that received live tumor cells and 3F8 survived significantly longer than control mice upon IV rechallenge with EL4 tumor cells (p<0.05). Moreover, when yeast beta-glucan was included as an adjuvant in the immunization, substantial antibody response and tumor protection were achieved. Mice that received live tumor cells mixed with 3F8 and yeast beta-glucan survived significantly longer than mice that received live tumor cells and 3F8, upon IV rechallenge (p<0.001, FIG. 4). The dosage of yeast beta-glucan also correlated with antibody titer against EL4 tumor cells (FIG. 5) and survival (FIG. 6) upon subsequent rechallenge.

Figure 7:
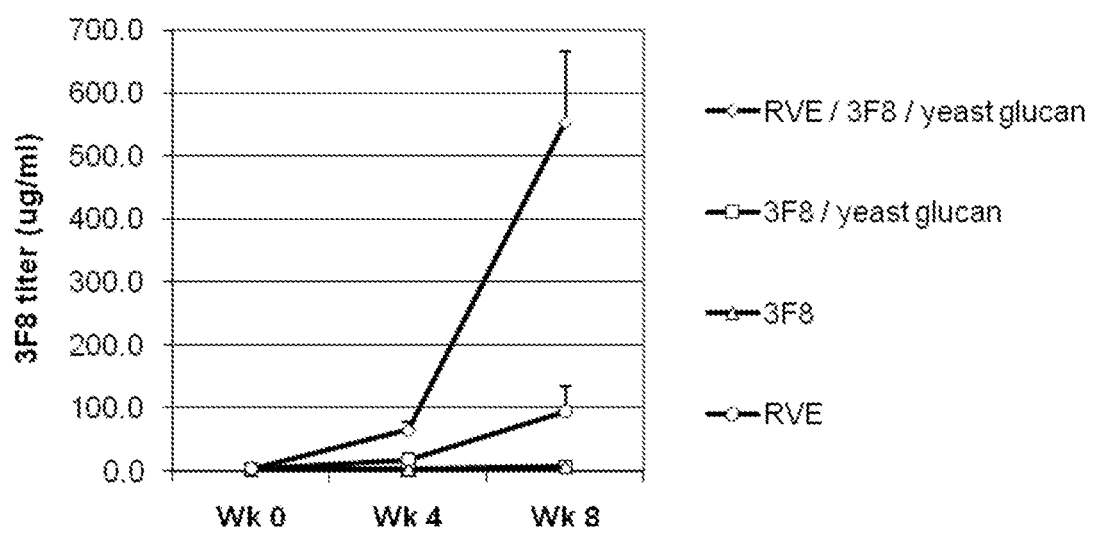
FIG. 7 shows mouse serum antibody response after Balb/c mice were subcutaneously immunized with a mixture of RVE tumor cells ($2 \times 10^6$), tumor-reactive Ab 3F8 (50 µg) and yeast beta-glucan (2 mg). Mouse serum antibody titers were assayed by FACS using a standard curve generated by 3F8. Data represent mean+standard error for 5 mice. RVE tumor cells with 3F8 and yeast glucan generates a significantly higher antibody response than RVE alone (p<0.001).

The anti-EL4 tumor response induced by sc EL4+3F8+yeast beta-glucan immunization was not directed against GD2 because the resulting mouse serum did not react with the GD2-positive neuroblastoma cell line LAN-1. Further, the antibody response towards sc EL4+3F8+yeast beta-glucan was specific to EL4 tumors because the resulting mouse serum did not react with a GD2-negative EL4 variant. When another GD2-positive lymphoma (RVE tumor cells) was mixed with 3F8 and yeast beta-glucan as a sc vaccine in the Balb/c mice, a strong anti-tumor antibody response was induced (FIG. 7). Protection from tumor challenge was not tested in this model because RVE was poorly clonogenic in immune deficient mice.

Accordingly, the yeast beta-glucan compositions of the present technology are useful in methods of enhancing the immunogenicity of whole cell tumor vaccines.

Example 2: Comparison of Yeast Beta-Glucans with Other Adjuvants

Figure 8:
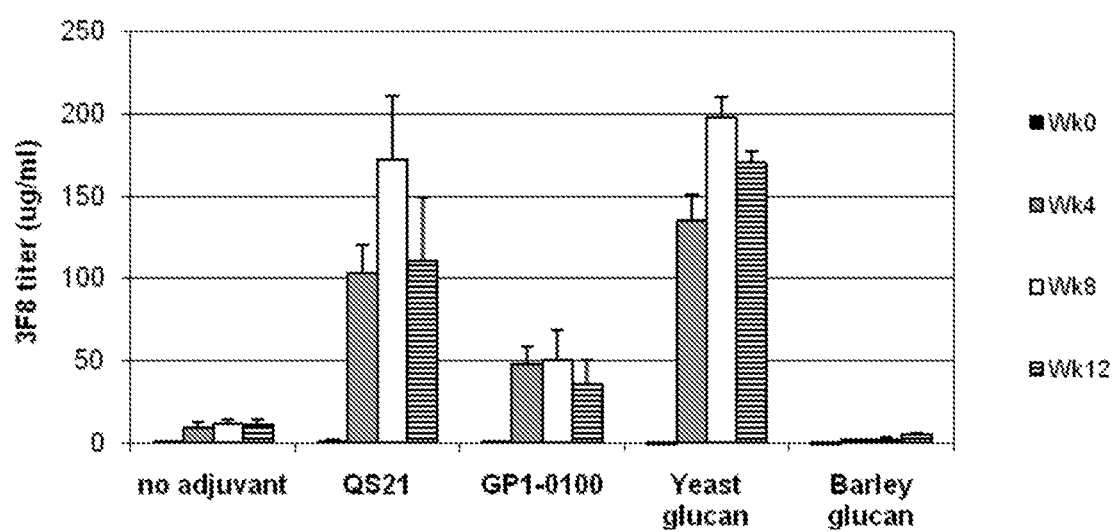
FIG. 8 shows mouse serum antibody response after C57BL/6 mice were subcutaneously immunized with GD2 (+) EL4 lymphoma ($5 \times 10^5$) in the presence of anti-GD2 antibody 3F8 (50 µg) plus an adjuvant selected from: QS21 (10 µg), GPI-0100 (100 µg), yeast glucan (2 mg) or barley glucan (2 mg). Mouse serum anti-tumor antibodies (in 3F8 equivalent units) were assayed by FACS against EL4 using a standard curve generated by 3F8. Data represent mean+ standard error for 5 mice. The adjuvant effect of yeast glucan on the EL4 whole cell tumor vaccine appeared to be comparable to that observed with QS21, and was significantly better than that observed in the no adjuvant control, GPI-0100 and barley glucan (p<0.001).

The effects of several different adjuvants in the sc EL4/3F8 vaccine regimen described in Example 1 were tested. QS21 (Bonam et al., Trends Pharmacol Sci 38:771-793 (2017)) and GPI-0100 are two saponin immunological adjuvants known to have maximal tolerated doses at 20 µg and 200 µg, respectively (Livingston et al., Vaccine 12:1275-1280 (1994)). C57BL/6 mice were immunized subcutaneously with GD2 (+) EL4 lymphoma tumor cells ($5 \times 10^5$) in the presence of anti-GD2 antibody 3F8 (50 µg) plus an adjuvant selected from: QS21 (10 µg), GPI-0100 (100 µg), yeast glucan (2 mg) or barley glucan (2 mg). Mouse serum anti-tumor antibodies (in 3F8 equivalent units) were assayed by FACS against EL4 using a standard curve generated by 3F8. Yeast glucan had an adjuvant effect that was comparable to QS21 and better than GPI-0100 whereas barley glucan had no adjuvant effect (FIG. 8).

Taken together, these results demonstrate that not all beta-glucans are capable of enhancing the immunogenicity of whole cell tumor vaccines. Accordingly, the yeast beta-glucan compositions of the present technology are useful in methods of enhancing the immunogenicity of whole cell tumor vaccines.

Example 3: Receptor-Dependence for Whole Tumor/Antibody/Beta-Glucan Vaccine Efficacy The importance of CD4 T cells, macrophages, and NK cells in the induction of in vivo antibody response to whole cell tumor vaccines and in tumor protection was tested. CD4 T cells were immunodepleted using 200 µg of anti-CD4 mAb L3T4 mAb iv on day-3, -2 and -1 before the start of the experiment and then once weekly throughout the experiment. Macrophages were immunodepleted using 0.5 mg of gadolinium chloride (Sigma-Aldrich, St. Louis MO) ip on day-2 and -1 and once weekly thereafter. NK cells were immunodepleted using 4 µl anti-asialo GM1 ip (Wako USA, Richmond VA) on day-6 and -3 and once weekly thereafter.

The efficacy of the whole tumor cell vaccine regimen in knock-out mice that were genetically deficient in one of the following was also evaluated: C3, CR2, CR3, FcRγ, FcγRIIB, or FcγRIII. Breeders of C3, CR3, FcγRIIb, FcγRIII knockout mice were obtained from Jackson Laboratory (Bar Harbor, ME). FcRγ knockout mice (deficient in the gamma chain subunit of the FcγRI, FcγRIII and FcERI receptors) were obtained from Taconic (Hudson, NY). CR2 knockout mice were provided by CBR, Harvard (Cambridge MA). Mice were maintained in a pathogen-free vivarium according to NIH Animal Care guidelines.

As shown in FIG. 9, the 3F8 and yeast glucan adjuvant effect required CD4 T cells, macrophages, and CR2 but did not require C3, CR3, or FcRγ. Further, the tumor vaccine studies described in Examples 1-3 demonstrate that cancer vaccines when given either intravenously or subcutaneously induced an anti-tumor antibody response that is protective against tumor rechallenge. This effect was further enhanced by administration of sc yeast beta-glucan but not barley glucan. Without wishing to be bound by theory, it is believed that the anti-tumor antibodies generated in this model function as opsonins to promote the immunogenicity of both human and murine tumor antigens and mAbs may enhance priming of effective tumor immunity.

Nascent endogenous anti-tumor antibodies in the naïve mouse were clearly inadequate because they did not protect mice from tumor challenge. Dead tumor cells could induce an antibody response, which was greatly enhanced when 3F8 was administered and when live tumor cells were present, suggesting that mAb treatment in the presence of an active tumor may aid in inducing tumor immunity. Without wishing to be bound by theory, it is believed that the induced antibodies likely bind epitopes distinct from GD2 (the target antigen for 3F8), thereby promoting antibody-dependent tumor cell cytotoxicity or the afferent arms of T-cell dependent tumor immunity.

Diaz de Stahl et al., J Exp Med 197:1183-90 (2003) reported that enhancement of antibody responses by IgG3 was significantly impaired in mice depleted of complement factor C3, whereas mice lacking the common Fc-receptor γ chain (FcRγ-/-) (resulting in reduced expression of FcγRI and lack of FcγRIII) and mice lacking FcγRIIB (FcγRIIB-/-), responded equally well to immunization with IgG3-complexed antigen as wild-type controls. In the current Examples, FcRγ, FcγRIII and FcγRIIB were also not required for an antibody response to whole cell tumor vaccines. However, unlike Diaz de Stahl et al. (2003), C3 is not required for an antibody response to whole cell tumor vaccines.

Accordingly, the yeast beta-glucan compositions of the present technology are useful in methods of enhancing the immunogenicity of whole cell tumor vaccines.

Example 4: The Importance of Beta-Glucan Structure and its Adjuvant Properties

In contrast to yeast beta-glucan, barley glucan had no adjuvant activity (FIG. 8). *Ganoderma lucidum* (GL, Lingzhi) polysaccharides, which contain the same branched beta-1,3-1,6-glucans as in yeast beta-glucan, are also immunogenic (Chan et al., Int Immunol 19:891-9 (2007). These observations are consistent with prior studies that show that only glucans of a certain molecular size show enhancement of anti-tumor antibody response (Cheung et al., Cancer Immunol Immunother 51:557-64 (2002) and Cheung and Modak, Clin Cancer Res 8:1217-23 (2002)).

Accordingly, the yeast beta-glucan compositions of the present technology are useful in methods of enhancing the immunogenicity of whole cell tumor vaccines.

Example 5: Adjuvant Effect of Oral Yeast Beta-Glucan in GD2-KLH Tumor Vaccine

GD2 and GD3 are examples of antigens that elicit a poor immunogenic response in human subjects. Occasional antibody responses against GD2 result after immunization with whole melanoma cells and 1-2 of 6 patients in previous trials produced antibodies (median titer 1/80) following immunization with GD2-KLH plus QS-21. QS-21 (Optimer Pharmaceuticals, Jersey City NJ), generated by fractionating a mixture of saponins from Quillaja *saponaria*, contains 2 isomers which are present in a ratio of 65% of the apiose form to 35% of the xylose form. GD3 is the least immunogenic of the gangliosides in humans. Lactone formation was found to significantly augment the immunogenicity of these gangliosides.

Figure 24:
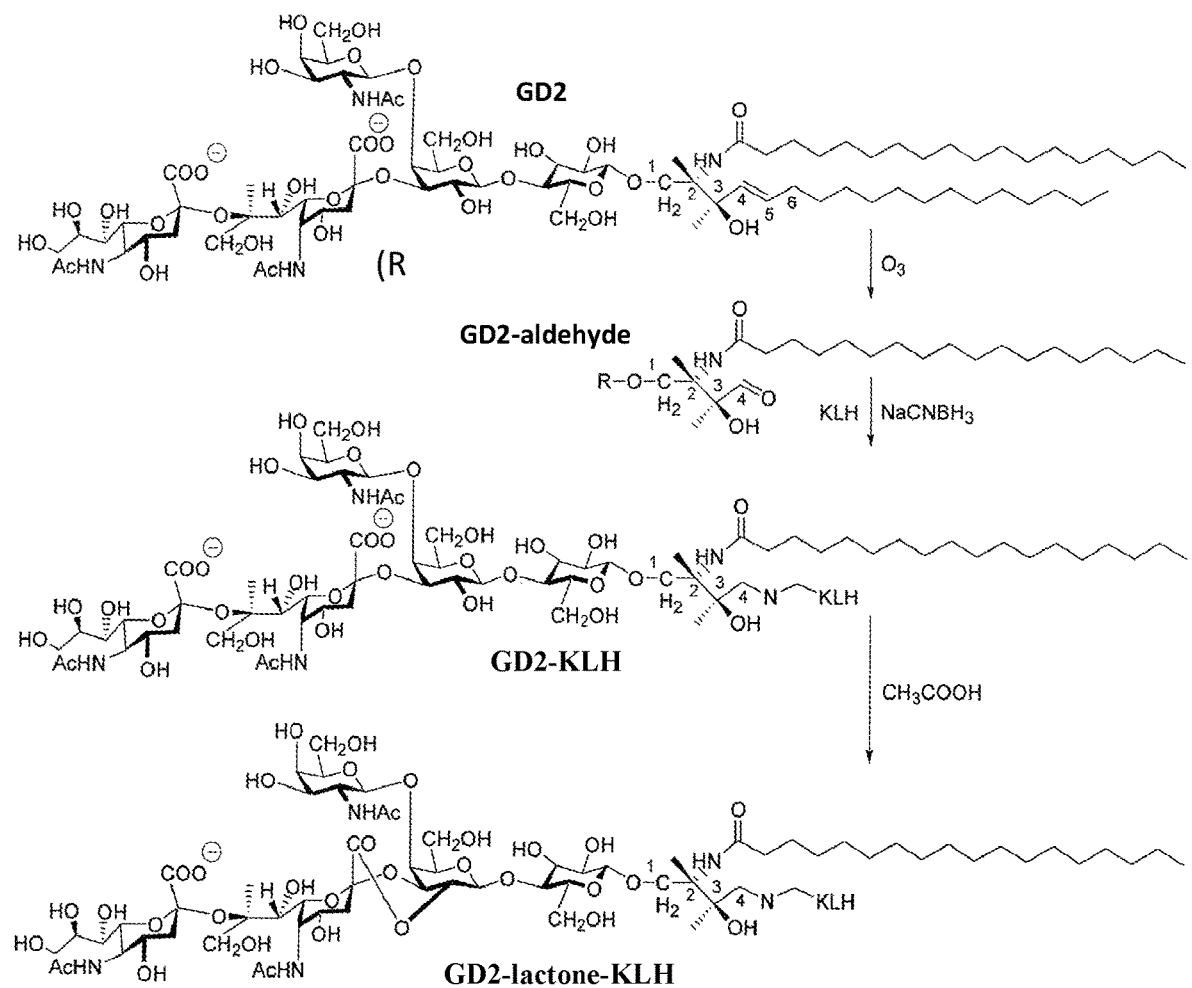
FIG. 24 shows a schematic of the chemical synthesis of a GD2-lactone-keyhole limpet hemocyanin (KLH) vaccine.
Figure 25:
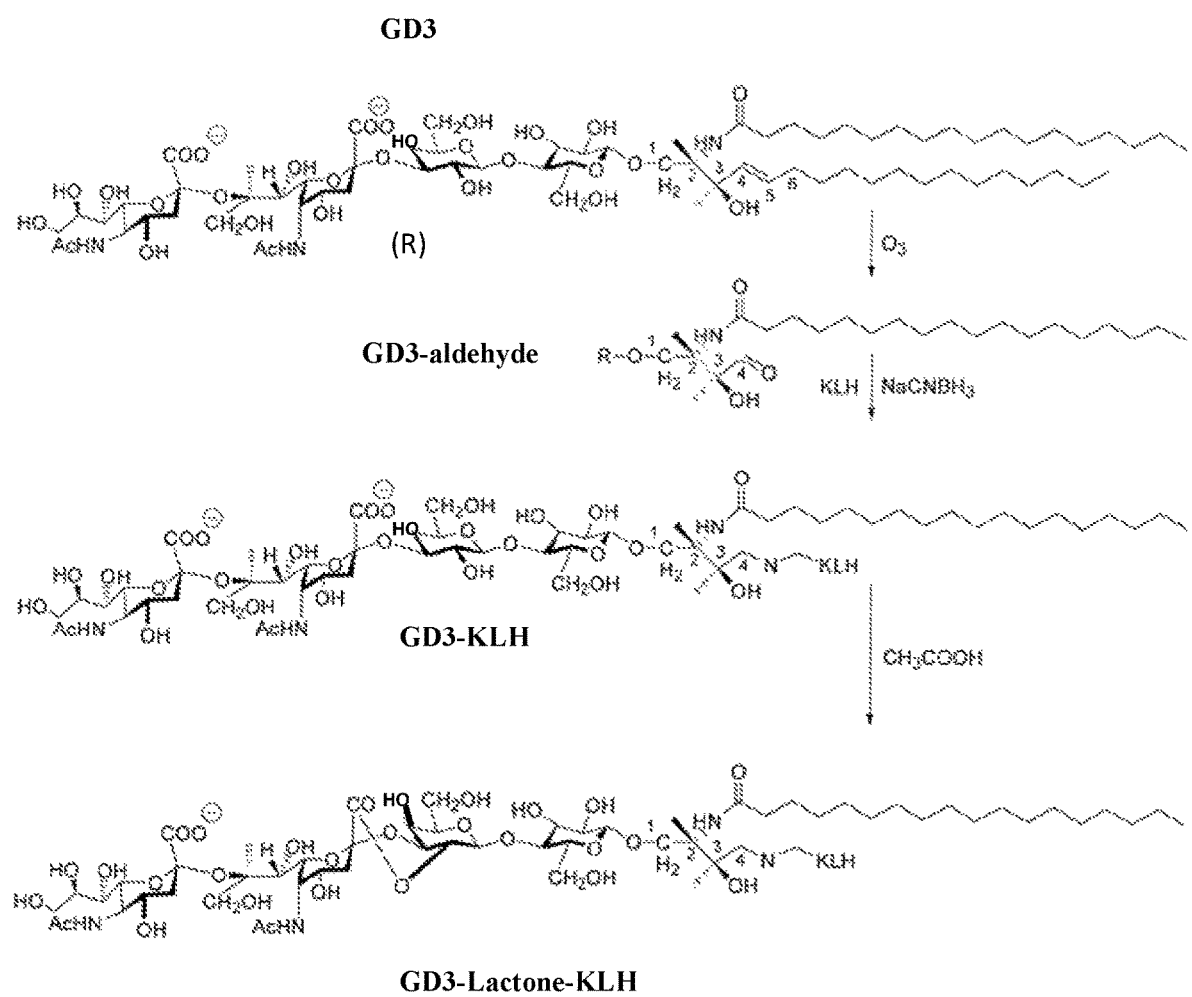
FIG. 25 shows a schematic of the chemical synthesis of a GD3-lactone-KLH vaccine.

FIG. 24 and FIG. 25 show the chemical synthesis of a GD2-lactone-keyhole limpet hemocyanin (KLH) and GD3-lactone-KLH, respectively. Briefly, the ceramide double bond of the gangliosides was cleaved using ozone and followed by introduction of an aldehyde group. The subsequent steps included direct coupling to amino lysyl groups on KLH by reductive amination. The lowest optimal dose for both GD3 lactone and GD2 lactone was 30 mcg per vaccine.

Figure 13:
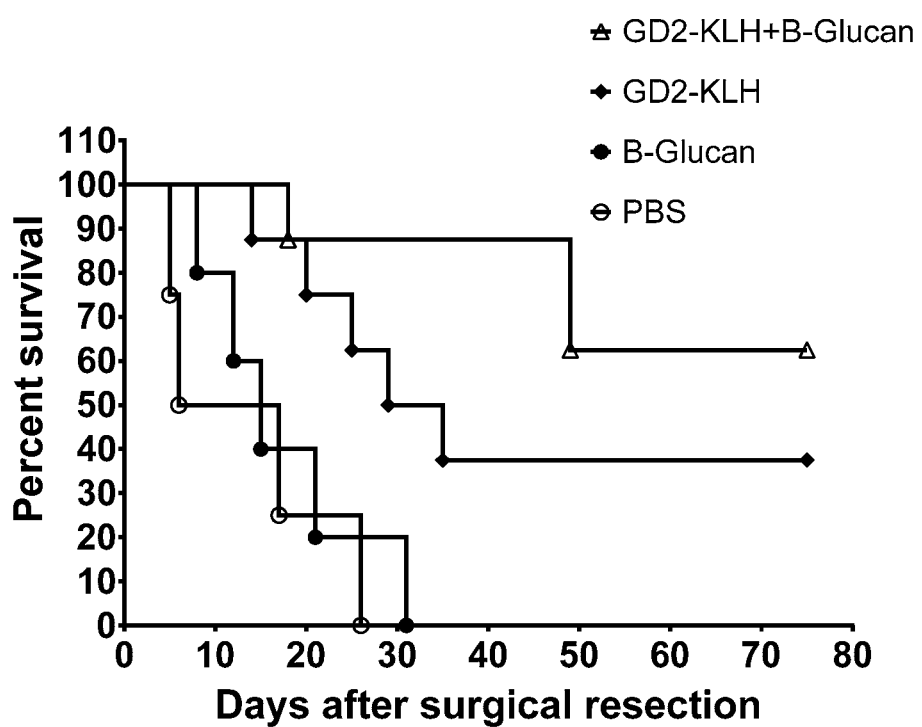
FIG. 13 shows the survival curves of mice in different treatment groups after GD2 (+) EL4 footpad tumor implantation (day-28), footpad amputation (day 0), GD2-KLH vaccine plus QS-21 adjuvant (days-4, 0, 3 and 16) and oral yeast beta-glucan adjuvant (days 1-20).

C57B1/6 mice were vaccinated with 3 μg of GD2-KLH and 20 μg of QS-21 before and after amputation of the foot pad tumor, in the presence or absence of daily 2 mg doses of orally administered yeast beta-glucan for 21 days. Mice receiving GD2-KLH vaccine had prolonged survival compared to PBS (FIG. 13). Further, the addition of beta-glucan further improved survival in mice receiving GD2-KLH vaccine, whereas beta-glucan by itself had no effect (FIG. 13).

Accordingly, the yeast beta-glucans of the present technology are useful in methods for enhancing the immunogenicity of poorly immunogenic antigen-specific vaccines (e.g., GD2-KLH or GD3-KLH) in a subject in need thereof.

Figure 14:
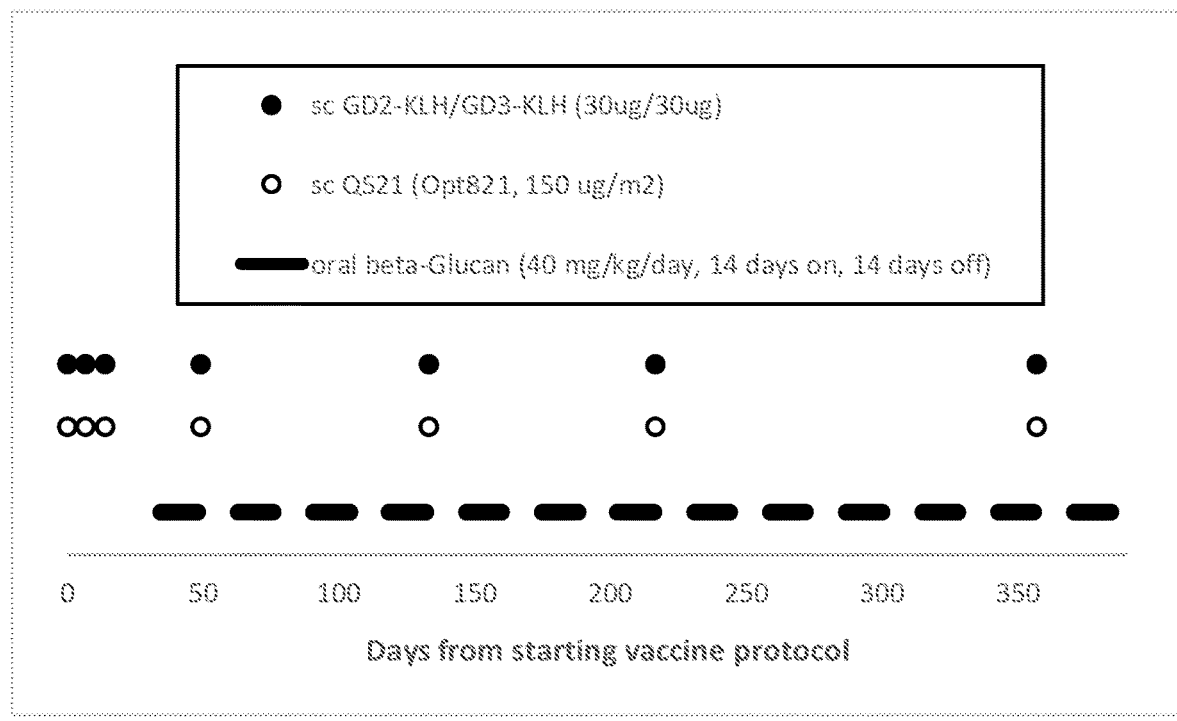
FIG. 14 shows the treatment schedule for administration of the GD2/GD3 bivalent vaccine.

Example 6: Phase I Trial of GD2/GD3 Bivalent Vaccine in High Risk Neuroblastoma (HR-NB) Patients in ≥2$^{nd}$ Remission Patients with neuroblastoma in ≥2nd complete/very good partial remission received vaccine subcutaneously (at weeks 1, 2, 3, 8, 20, 32 and 52). The bivalent vaccine contained 30 μg each of GD2 and GD3 stabilized as lactones and conjugated to the immunologic carrier protein keyhole limpet hemocyanin (KLH); and OPT-821, which was dose escalated as 50, 75, 100, and 150 μg/m$^2$ per s.c. injection. Oral beta-glucan administration (40 mg/kg/day, 14 days on/14 days off x 12 cycles) was started at week 6 (FIG. 14). The phase I study was completed with 15 patients because there was no dose-limiting toxicity at 150 μg/m$^2$ of OPT-821 (the dosing used in adults). 13 of 15 patients received the entire protocol treatment, including 12 patients who remained relapse-free at 24+to 39+ (median 32+) months and 1 patient who relapsed (single node) at 21 months. Relapse-free survival was 80%+10% at 24 months. 14 of 15 patients were still alive after 10 years. Vaccine and beta-glucan were well tolerated. 12 of 15 patients had antibody responses against GD2 and/or GD3. The disappearance of minimal residual disease was documented in 6 of 10 patients assessable for response.

Accordingly, the yeast beta-glucans of the present technology are useful in methods for enhancing the immunogenicity of poorly immunogenic antigen-specific vaccines (e.g., GD2-KLH or GD3-KLH) in a subject in need thereof.

Example 7: Phase II Trial of GD2/GD3 Bivalent Vaccine in HR-NB Patients in ≥2$^{nd}$ Remission In a Phase II trial, 7 doses of 60 μg of GD2-KLH/GD3-KLH conjugate vaccine mixed with 150 μg/m$^2$ of adjuvant OPT-821 (FIG. 14) were administered subcutaneously in an outpatient setting over one year in 84 patients with HR-NB in ≥2$^{nd}$ remission. Oral yeast beta-glucan (40 mg/kg/day, 14 days on/14 days off x 10 months) was started at week 6 to enhance antibody mediated cytotoxicity. Progression-free survival (PFS) and overall survival (OS) were estimated by Kaplan Meier analyses.

All 84 patients had prior relapse, 57 treated were in 2nd remission, 18 were in 3rd remission, and the rest were in the 4th to 7th remission. All patients had prior exposure to either mouse 3F8 (63%), and/or human 3F8 (57%), and/or dinutuximab (46%). Median follow-up was 19 months; PFS was 54%+6% and OS was 90%+5% at 2 years with no >grade 3 toxicities. Serum anti-GD2 and anti-GD3 IgGI antibodies were measured using ELISA at serial time points, integrated, and expressed as area-under-the-curve per month. Anti-GD2 titer was positive pre-vaccine in 13% of patients, and positive post-vaccine in 83% of patients. Anti-GD3 titer was positive pre-vaccine in 29.4% of patients, and positive post-vaccine in 70.4% of patients.

Figure 15:
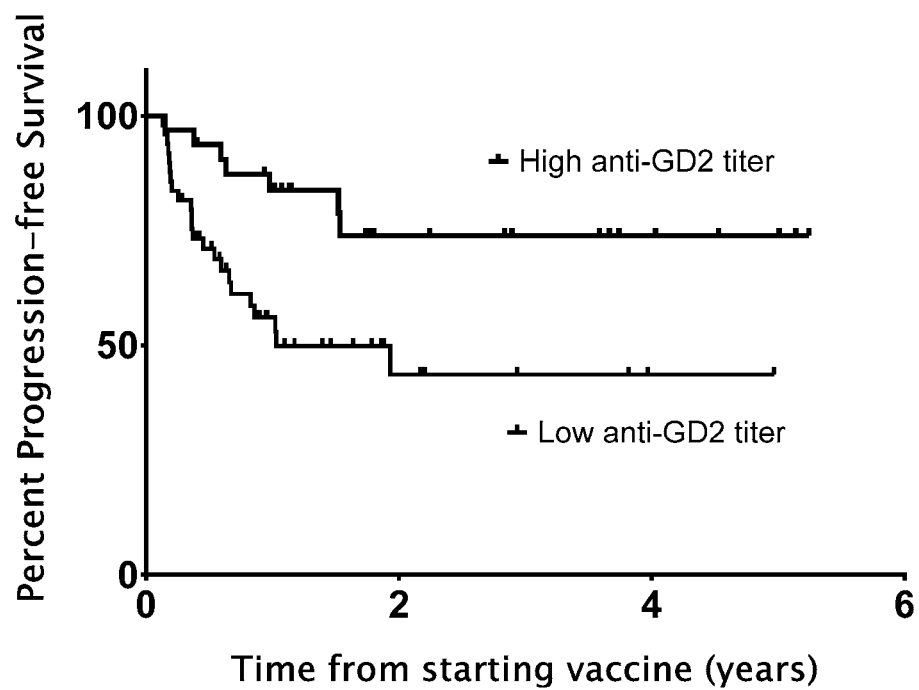
FIG. 15 shows the progression-free survival curves of patients treated in ≥2nd remission. Patients with high anti-GD2 titer (top ~50% of patient population) have superior progression-free survival compared to the rest.
Figure 16:
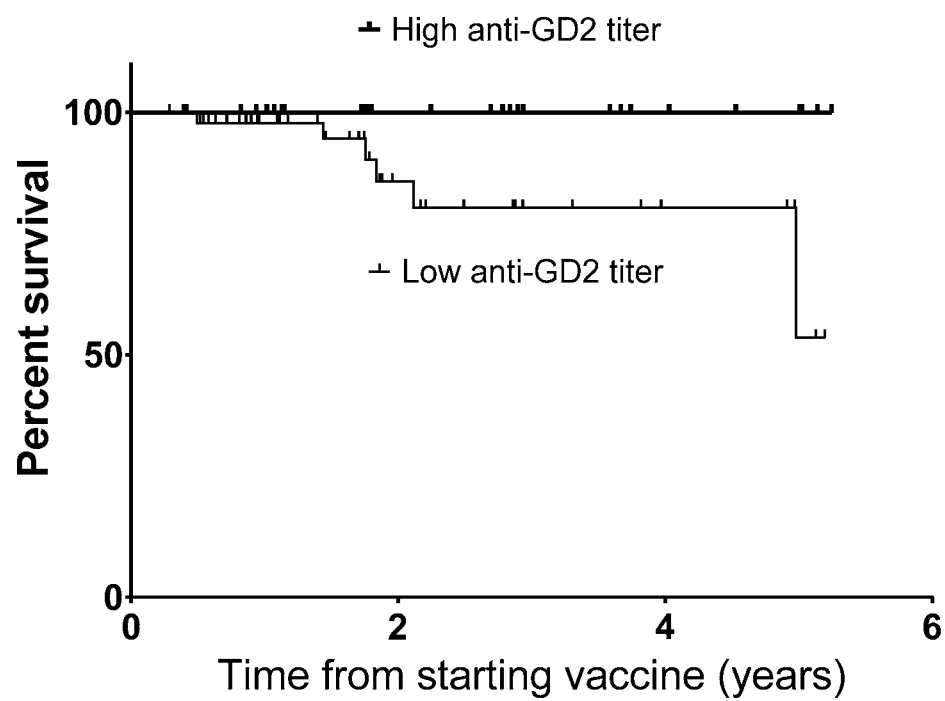
FIG. 16 shows the overall survival curves of patients treated in ≥2nd remission. Patients with high anti-GD2 titer (top ~50% of patient population) have superior overall survival compared to the rest (bottom ~50% of patient population).

The observed adjuvant effects of yeast beta-glucan were correlated with an improved anti-tumor response. The resulting anti-GD2 antibody titer did not result in any patient having pain or neuropathy. There was no correlation between pre-vaccine and post-vaccine titer. Anti-GD2 antibody titer >120 ng/ml/month was prognostic for improved PFS and OS (p-0.03 and 0.018, respectively, FIG. 15 and FIG. 16). In contrast, the resulting anti-GD3 response had no prognostic significance for survival. Moreover, the concurrent improvement of both anti-GD2 and anti-GD3 antibody titers in patients demonstrates that no antigenic competition is observed when a mixture of antigens is used with the yeast beta-glucan compositions of the present technology.

There was no impact on patient outcome based on age at diagnosis, time from diagnosis, MYCN amplification, number of prior relapses, pre-vaccine anti-GD2 antibody therapy, as well as pre-vaccine anti-GD2 serum titer. A similar clinical trial was also performed in patients in their first remission with shorter follow-up and fewer events (relapse or death).

Accordingly, the yeast beta-glucans of the present technology are useful in methods for enhancing the immunogenicity of poorly immunogenic antigen-specific vaccines (e.g., GD2-KLH or GD3-KLH) in a subject in need thereof.

Figure 17:
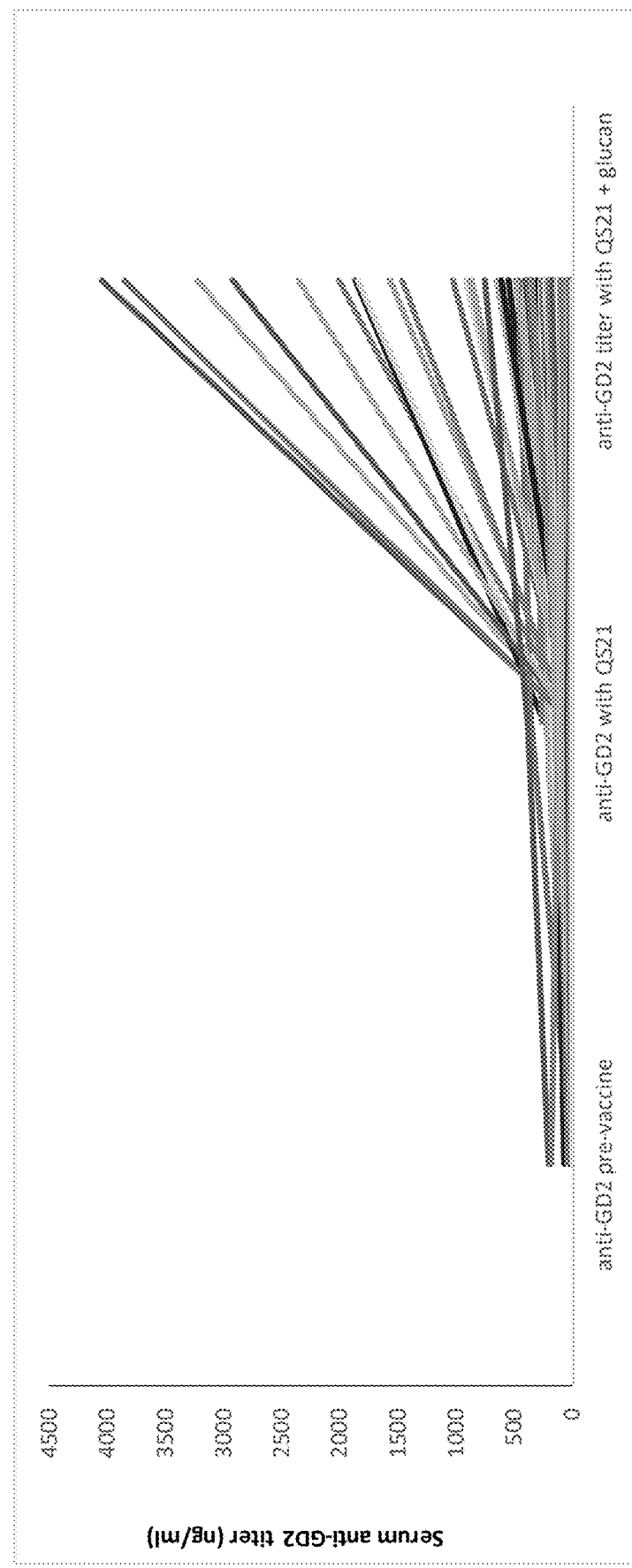
FIG. 17 shows a graphical representation of serum anti-GD2 titer in patients before and after initiating oral administration of yeast beta-glucan in individual patients receiving the GD2/GD3 bivalent vaccine.
Figure 18:
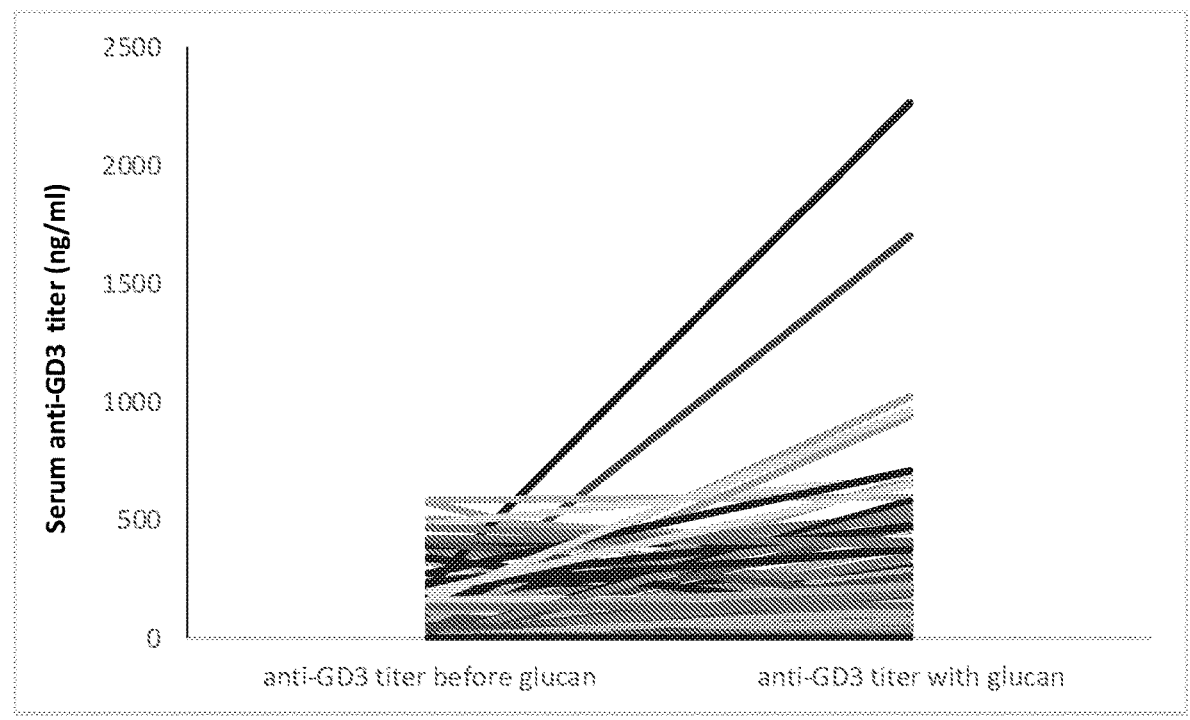
FIG. 18 shows a graphical representation of serum anti-GD3 titer in patients before and after initiating oral administration of yeast beta-glucan in individual patients receiving the GD2/GD3 bivalent vaccine.
Figure 19:
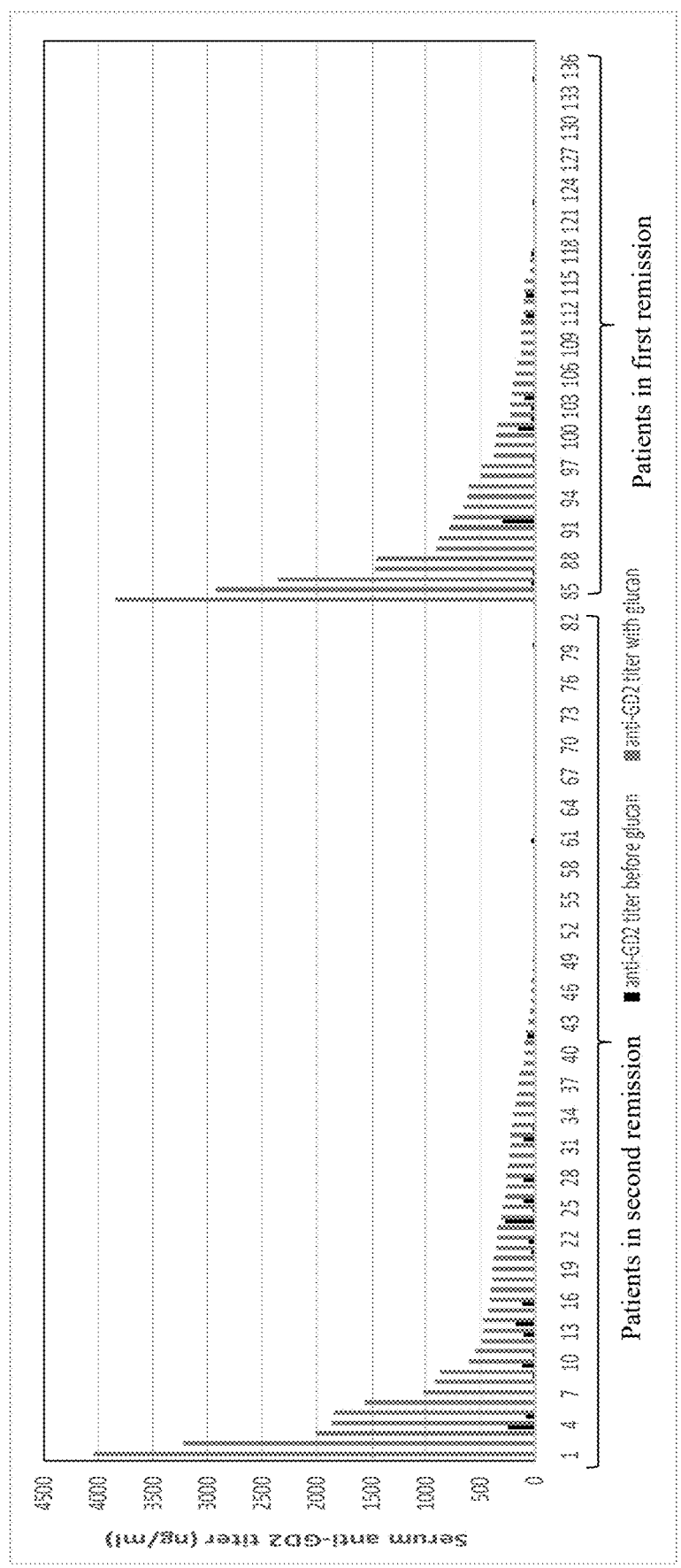
FIG. 19 shows serum anti-GD2 titer before and after initiating oral administration of yeast beta-glucan in first or second remission patients receiving the GD2/GD3 bivalent vaccine. Black=pre-glucan, Grey=on-glucan. Patients were sorted in descending order of anti-GD2 titer while on oral yeast beta-glucan.
Figure 20:
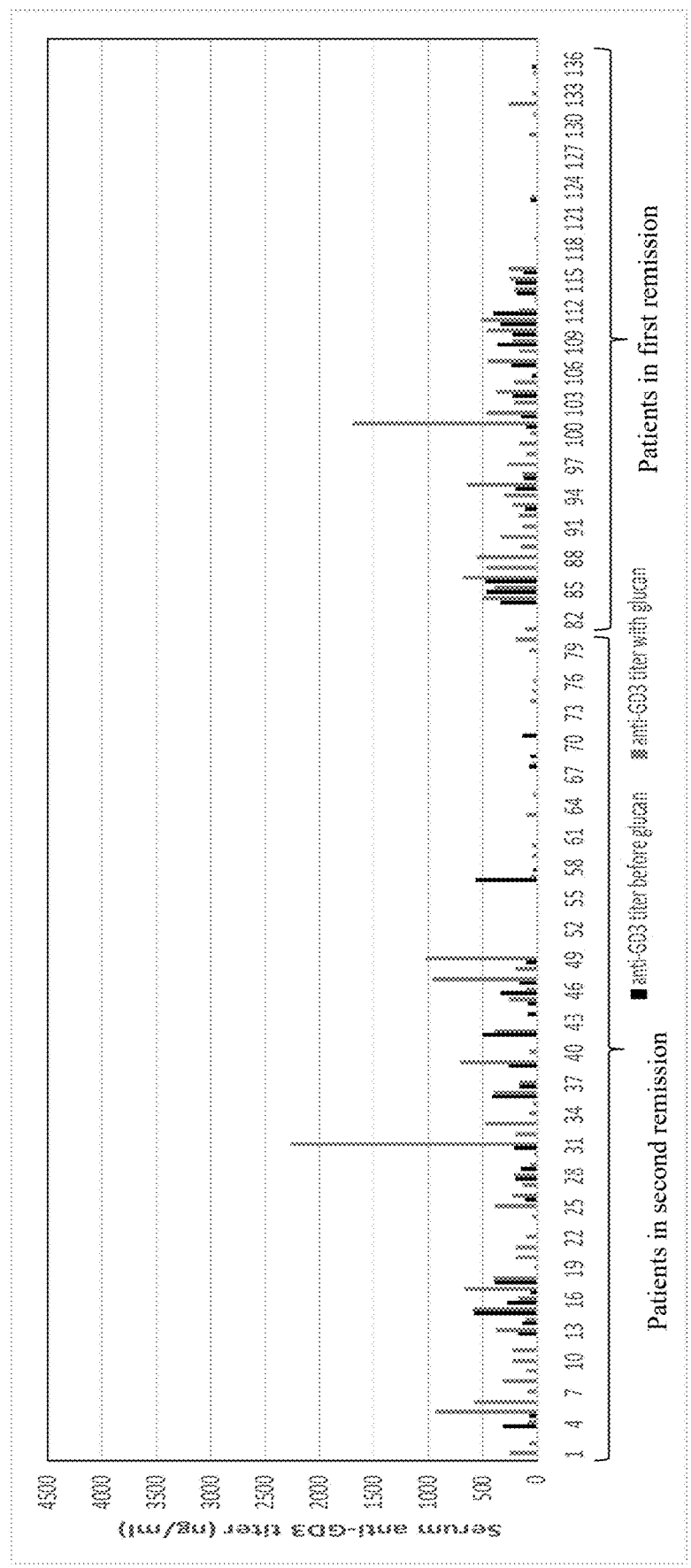
FIG. 20 shows serum anti-GD3 titer before and after initiating oral administration of yeast beta-glucan in first or second remission patients receiving the GD2/GD3 bivalent vaccine. Black=pre-glucan, Grey=on-glucan. The order of the patients is the same as in FIG. 19.
Figure 21:
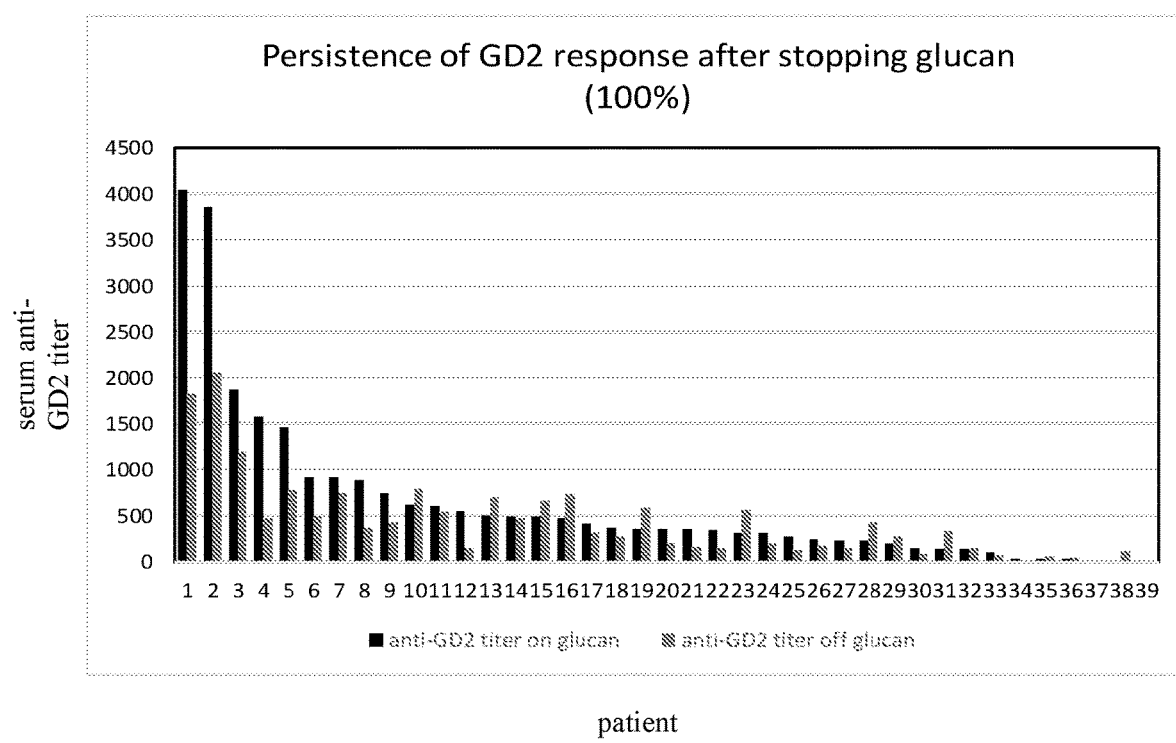
FIG. 21 shows the persistence of serum anti-GD2 titer in patients that have completed 7 cycles of vaccination and are either on and off yeast beta-glucan. Black=while on glucan, Grey=off glucan. Patients were sorted in descending order of peak anti-GD2 titer while on glucan.

Example 8: Oral Yeast Beta-Glucan Increased Anti-GD2 and Anti-GD3 Antibody Titers in $1^{st}$ and $\geq 2^{nd}$ Remission Patients Receiving GD2/GD3 Vaccine Serum anti-GD2 and anti-GD3 titers (FIG. 17 and FIG. 18, respectively) were monitored in individual patients using ELISA at serial time points, integrated, and expressed as area-under-the-curve per month. Serum anti-GD2 antibody rose minimally with vaccine/QS21 during the first 5 weeks; from 8+3 to 35+7 (p=0.007). As soon as oral glucan was initiated, anti-GD2 antibody titer (FIG. 17) increased by 10-fold (from 35+7 to 367+61 (p=2×10$^{-7}$) in the combined group of patients treated in first remission and in $\geq 2^{nd}$ remission. Anti-GD3 titers (FIG. 18) also increased after initiation of oral glucan, but not as robustly as the anti-GD2 titers. The pre-glucan and on-glucan anti-GD2 titers in individual patients treated in $\geq 2^{nd}$ and $1^{st}$ remission are summarized in FIG. 19. The pre-glucan and on-glucan anti-GD3 titers in individual patients treated in $\geq 2^{nd}$ and $1^{st}$ remission are summarized in FIG. 20. The anti-GD2 titer persisted for up to 2 years even when the individual patient was no longer receiving oral glucan (FIG. 21). Anti-GD3 titer was also monitored in these patients (FIG. 20) and as noted above, anti-GD3 response also increased after oral glucan, though not as substantially as the anti-GD2 response. Further, there was no correlation with survival (PFS or OS), suggesting that GD3, unlike GD2, may not be the right target for antibody therapy of neuroblastoma.

Accordingly, the yeast beta-glucans of the present technology are useful in methods for enhancing the immunogenicity of poorly immunogenic antigen-specific vaccines (e.g., GD2-KLH or GD3-KLH) in a subject in need thereof.

Example 9: Oral Yeast Beta-Glucan was Associated with a Diversification of the Gut Microbiome Stool specimens were obtained from neuroblastoma patients prior to, during, and following the end of oral yeast glucan treatment (40 mg/kg/day, 14 days on/14 days off). The stool samples were analyzed using 16S ribosomal RNA gene sequencing. The microbiota composition in this cohort was compared to a previously analyzed population of healthy twin pairs using t-Distributed Stochastic Neighbor Embedding (tSNE) visualization. It was also compared to stool samples from patients during temporal phases of their neuroblastoma treatment. Diversity was analyzed using the Simpson's Diversity Index. Microbiota maturity was determined using a Random Forest model approach. Pre-treatment samples demonstrated no significant dysbiosis, with predicted microbiota maturity falling within six months of chronologic age. Dysbiosis developed in all patients receiving induction chemotherapy, with both loss of diversity and domination by *Enterococcus faecium*. Microbiota immaturity was observed in all patient samples during induction and consolidation, with predicted microbiota age below 12 months, independent of chronologic age. In children analyzed after completion of standard therapy for HR-NB, gut microbiota continued to be immature, despite overall improvement in intestinal diversity. In this group, predicted microbiota age ranged 8-18 months, for chronologic ages of 3-9 years. When patients started on oral glucan, there was a consistent diversification of the microbiome and normalization of the intestinal dysbiosis.

The intestinal microbiome of healthy individuals is dominated by bacterial species from the Bacteriodetes and Firmicutes phyla, with representation from additional less dominant phyla, namely Actinobacteria, Fusobacteria, Proteobacteria and Verrucomicrobia. Based on the disclosed preclinical and clinical data, without wishing to be bound by theory, it is believed that oral yeast beta-glucan may promote diversification of the microbiome, which in turn strongly enhances the immune response to both carbohydrate and protein antigens administered as sc vaccines. This enhancement was extremely effective against tumor recurrence and protected patients from relapse or death from cancer, even in children immunocompromised from prior chemoradiotherapy. As described in Examples 6-8, the yeast beta-glucan was completely safe when administered over a period of 46 weeks and the antibody titer induced persisted for at least 2 years even when yeast beta-glucan was ceased.

Accordingly, the yeast beta-glucans of the present technology are useful in methods for increasing gut microbiome diversity in a subject in need thereof.

Example 10: In Vivo Tumor Cytotoxicity of Botanical Adjuvants in the Presence of Anti-tumor Antibodies Tumor therapy. SCID mice (Jackson Lab, Bar Harbor ME) were first implanted subcutaneously in the flank area with Ramos tumor cells (a human lymphoma cell line; Pagel et al., Blood 108:328-36 (2006)) freshly harvested from culture and suspended in 100 µl matrigel (BD Biosciences, Billerica MA). When small palpable tumors started to appear (6-8 mm size), mice were randomly separated into treatment groups of 5 mice each. Mice were then given either oral botanical adjuvant, intravenous Rituxan mAb, or oral botanical adjuvant plus Rituxan mAb for 3 weeks. MAb was given twice a week through the tail vein. 2 mg of the tested botanical adjuvant (20 mg/ml solution or suspension in LPS-free water) was given by intragastric injection for 5 times a week. Tumor sizes (length and width) were measured twice a week with calipers. Mice were sacrificed when tumors were larger than 20 mm in length. For each botanical adjuvant, two endpoints were obtained: (1) positive anti-tumor effect [defined as statistically different from control group (treated with antibody alone)] and (2) anti-tumor index defined as (Mean tumor growth rate in mice treated with antibody alone)/(Mean tumor growth rate in mice treated with botanical adjuvant+antibody). The tested botanical adjuvants included barley (Megazyme International Ireland Ltd, Ireland) and yeast (Biotec Pharmacon, Tromso, Norway) beta-glucans, *Astragalus membranaceus* water extract, *Astragalus membranaceus* 50% ethanol extract (Institute of Chinese Medicine (ICM), Hong Kong), *Astragalus membranaceus* 95% ethanol extract (ICM, Hong Kong), *Coriolus versicolor* water extract (ICM, Hong Kong), *Coriolus versicolor* polysaccharide-peptide (PSP) (ICM, Hong Kong), *Coriolus versicolor* protein bound polysaccharide-K (PSK) (ICM, Hong Kong), and Turmeric Hydro-ethanol (HE) extract (New Chapter, Median, North Dakota).

Figure 22:
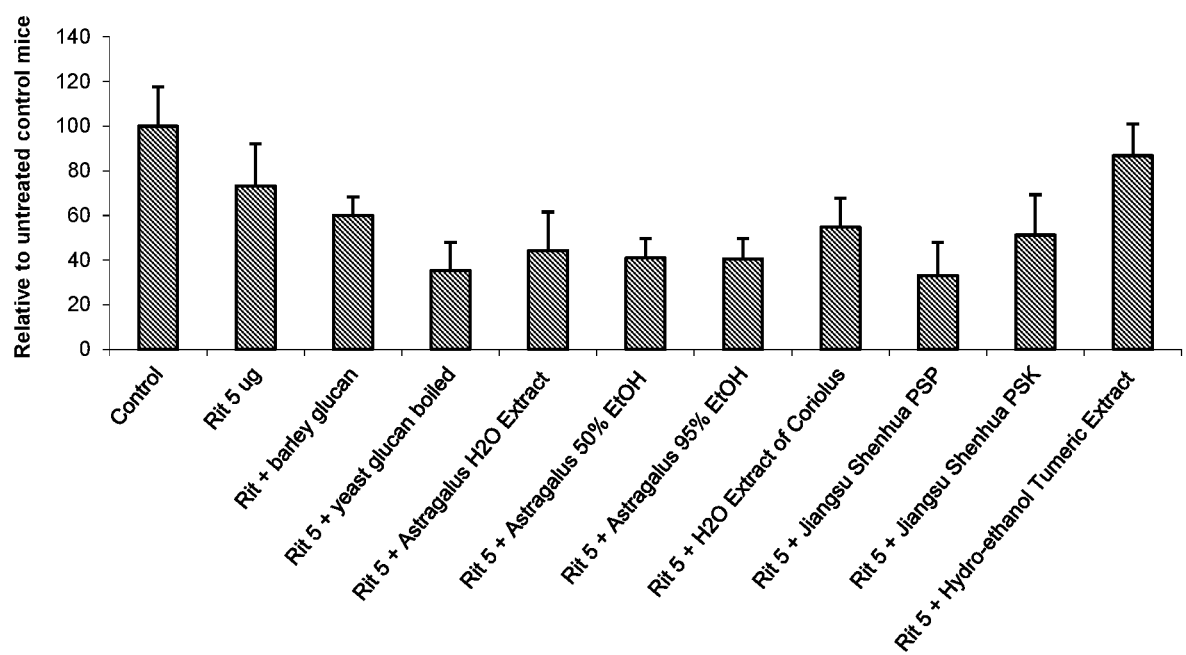
FIG. 22 shows a graphical representation of the relative tumor size of established Ramos xenografts in SCID mice on day 21 after treatment with Rituxan (Rit) and different beta-glucan adjuvants.

Results. The human lymphoma Ramos was very sensitive to rituximab mAb (Rituxan) in vivo. Even at 5 µg dose, 30% of tumor growth was suppressed by Rituxan alone. When intravenous Rituxan was combined with oral botanical adjuvants, yeast glucan and *Coriolus versicolor* polysaccharide-peptide (PSP) elicited the strongest adjuvant effect, followed by *Astragalus membranaceus*. PSK (protein bound polysaccharide-K) and *Coriolus versicolor* water extract were less effective as adjuvants, whereas turmeric was totally ineffective (FIG. 22). The anti-tumor potency of the various botanical adjuvants tested is also summarized in FIG. 23.

Taken together, these results demonstrate that not all botanical adjuvants are equally effective in enhancing the immunogenicity of cancer vaccines. Accordingly, the yeast beta-glucans of the present technology are useful in methods of enhancing the immunogenicity of cancer vaccines.

Example 11: Induced Anti-GD2 Titer Following Oral Beta Glucan Strongly Correlates with Survival in Patients with High Risk Stage 4 Neuroblastoma (HR-NB)

7 doses of 60 μg of GD2-KLH/GD3-KLH conjugate vaccine mixed with 150 μg of adjuvant OPT821 were administered subcutaneously in an outpatient setting for over one year in 230 patients with HR-NB. Oral yeast beta-glucan at 40 mg/kg/day ×2 weeks q month×10 months was included to enhance antibody mediated cytotoxicity. Progression-free survival (PFS) and overall survival (OS) were estimated by Kaplan Meier analyses.

Results. 230 patients were accrued and treated with vaccine: 15 in phase I (group 1) and the rest in the phase II expansion. In the phase II expansion, 102 patients (group 2) were treated in ≥$2^{nd}$ remission nonrandomized fashion, and 34 (group 3) in the recent randomized extension. 78 patients (group 4) were treated in $1^{st}$ remission. A preliminary analysis showed that: (1) PFS of 51%+5%, longest followup at 102 months from starting vaccine among ≥$2^{nd}$ remission nonrandomized group, and 76%+6% among first remission group followup at 78 months from starting vaccine; (2) OS was 79%+9% and 98%+2%, respectively; (3) both IgM anti-GD2 antibody and IgG anti-GD2 antibodies were induced and high titer strongly correlated with both PFS and OS; (4) IgM anti-GD2 antibody titer was prognostic independently of IgG anti-GD2; (5) both IgM and IgG titers increased by 10-fold coinciding with the initiation of oral glucan; (6) both IgM and IgG persisted after vaccine was completed and glucan was stopped; (7) both IgM and IgG anti-GD3 antibodies were stimulated by the GD3 vaccine and further elevated by glucan, but neither IgM or IgG anti-GD3 titer correlated with patient outcome.

These results confirmed the safety of GD2-KLH/GD3-KLH vaccine and the impact of anti-GD2 seroconversion on PFS and OS. Both IgM (responsible for complement mediated cytotoxicity, complement dependent cell mediated cytotoxicity and complement dependent cell mediated phagocytosis) and IgG (responsible for NK-antibody cell mediated cytotoxicity (ADCC) and myeloid-ADCC) titers are enhanced by oral glucan and persist after the completion of vaccine and completion of oral glucan.

Accordingly, the yeast beta-glucans of the present technology are useful in methods for enhancing the immunogenicity of poorly immunogenic antigen-specific vaccines (e.g., GD2-KLH or GD3-KLH) in a subject in need thereof.

Example 12: Evaluation of Oral Beta-glucan Induced Antibody Response with the Different Influenza Vaccine Constructs A major focus for influenza (Flu) vaccine is the continuous need for development of highly immunogenic, yet safe, vaccines that induce a sufficient immune response against a shifting spectrum of target antigens. Examples of commercially available Flu vaccines include (1) inactivated and minimally purified (Fluzone®, Sanofi, Paris, France), (2) partially purified (Fluarix®, GSK, Brentford, United Kingdom) or (3) recombinant hemagglutinin (HA) protein (Flublok®, Protein Sciences, Meriden, CT) vaccines, which serve as ideal vehicles to test the effect of adjuvant or immunomodulators. See Table 2

TABLE 2

| | Comparison of Flu Vaccines | | |
|---|---|---|---|
| Vaccine | Flublok® Quadrivalent | Fluzone® Quadrivalent | Fluarix™ Quadrivalent |
| Company Name | Protein Sciences | Sanofi | GSK |
| Preservative | None | Preservative | None |
| Mode of vaccination | Intramuscular | Intramuscular | Intramuscular |
| Age | 18 years of age and older | 36 months of age and older | 3 years of age and older |
| Number of injection | One 0.5 mL dose | One 0.5 mL dose | One 0.5 mL dose |
| | Recombinant purified Hemagglutinin (HA) protein from Four influenza viruses | Influenza virus are concentrated and purified in a linear sucrose density gradient solution using a continuous flow centrifuge. Antigens from the Four strains included in the vaccine are produced separately and then combined to make the quadrivalent formulation. | Each of the Four influenza viruses is separately concentrated and purified by zonal centrifugation using a linear sucrose density gradient solution containing detergent to disrupt the viruses. |
| Appearance | Sterile, Clear and Colorless solution | Sterile, Clear and slightly opalescent in color. | Sterile, colorless, and slightly opalescent suspension |
| Formulations | 180 mcg HA/0.5 mL dose (45 mcg HA from each of 1. A/Michigan/45/2015 (H1NI) 2. A/Hong Kong/4801/2014 (H3N2) | 60 mcg HA contains 15 mcg of 4 influenza virus strains: 1. A/Michigan/45/2015 X-275 (H1N1) 2. A/Hong Kong/4801/2014 X-263B (H3N2) | 60 mcg HA contains 15 mcg of 4 influenza virus strains: 1. A/Singapore/GP1908/2 015 (H1N1) IVR-180 (an A/Michigan/45/2015 (H1N1) pdm09-like |

TABLE 2-continued

Comparison of Flu Vaccines

| Vaccine | Flublok ® Quadrivalent | Fluzone ® Quadrivalent | Fluarix ™ Quadrivalent |
|---|---|---|---|
| | 3. B/Brisbane/60/2008<br>4. B/Phuket/3073/2013 | 3. B/Phuket/3073/2013 (B Yamagata lineage)<br>4. B/Brisbane/60/2008 (B Victoria lineage). | virus).<br>2. A/Hong Kong/4801/2014 (H3N2) NYMC X-263B.<br>3. B/Brisbane/60/2008.<br>4. B/Phuket/3073/2013. |
| | 4.4 mg Sodium Chloride<br>0.195 mcg NaH$_2$PO$_4$<br>1.3 mg Na$_2$HPO$_4$<br>25.7 mcg Tween 20 | 25 mcg mercury<br>Sodium phosphate-buffered isotonic sodium chloride solution<br><100 mcg Formaldehyde<br><250 mcg Octylphenol ethoxylate | ≤0.115 mg octoxynol-10 (TRITON ® X-100)<br>≤0.135 mg α-tocopheryl hydrogen succinate ≤0.550 mg polysorbate 80 (TWEEN 80)<br>≤0.0016 mcg hydrocortisone<br>≤0.15 mcg gentamicin sulfate<br>≤0.050 mcg ovalbumin<br>≤5 mcg formaldehyde<br>≤65 mcg sodium deoxycholate |

Recombinant protein vaccines are typically associated with lower immunogenicity and, therefore, the need for repeated vaccinations plus a 3-fold higher vaccine dose compared to inactivated vaccines. See, e.g., Christensen, Human Vaccines & Immunotherapeutics, 12 (10): 2709-2711 (2016); Blanchfield et al., Influenza and Other Respiratory Viruses 8 (6), 628-635 (2014); Mazor et al., Proc. Natl. Acad. Sci. U.S.A. 111 (23): 8571-8576 (2014); and Onda et al., Proc. Natl. Acad. Sci. U.S.A. 105 (32): 11311-11316 (2008). Immunological adjuvants or immunomodulators that increase the effectiveness of these Flu vaccines (especially recombinant Flu HA protein vaccines) without compromising their favorable safety profile would have significant market potential.

with either Fluzone® (Sanofi Pasteur, Paris, France), FluArix™ (GSK, Brentford, United Kingdom) or Flublok® (Protein Sciences, Meriden, CT) at 1.5 mcg per mouse on Day 1 and Day 14. Beta-glucan was administrated orally on Day 1-5, 8-12, 15-19 and 22-16. Mice vaccinated with Flu vaccine alone served as positive control. Mice were bled on days 0, 14, 21, 28, 35, and then once every 4 weeks. All sera obtained on 0, 14, 21, 28, and 35 were tested by hemagglutination inhibition assay (see Table 3), the gold standard for measuring serologic responses to Flu or Flu vaccines. Antibody titers against HA have long been known to correlate with protection against Flu infections.

TABLE 3

| Vaccine | Conc/vial | Human | | Mouse | | Beta-glucan | Bleeding Schedule |
|---|---|---|---|---|---|---|---|
| | | Dose | Vaccination Schedule | Dose | Vaccination Schedule | | |
| FluArix ™ | 60 µg | 60 µg | 1 vaccine (on Day 1) | 1.5 µg | Day 1 & 14 | Day 1-5<br>Day 8-12<br>Day 15-19<br>Day 22-26 | Day 0, 14, 21, 28, 35, 63*, 91*, and 119*<br>(*once in 4 weeks) |
| Flublok ® | 180 µg | 180 µg | 1 vaccine (on Day 1) | 1.5 µg | Day 1 & 14 | | |
| Fluzone ® | 180 µg | 180 µg | 1 vaccine (on Day 1) | 1.5 µg | Day 1 & 14 | | |

Each Flu vaccine contains 4 antigens

FluArix ™: 60 µg/0.5 ml (each antigen at 15 µg/0.5 ml)

Flublok ®: 180 µg/0.5 ml (each antigen at 45 µg/0.5 ml)

Fluzone ®: 60 µg/0.5 ml (each antigen at 15 µg/0.5 ml)

One dose (1.5 µg) of each vaccine was tested with or without beta-glucan (BG). Five mice per group (6 groups × 5 mice = 30 total mice)

Methods. To determine whether oral administration of yeast beta-glucans could enhance the immunogenicity of Flu vaccines, beta-glucan induced antibody response was assessed using hemagglutination inhibition (HI) as endpoints. Groups of mice were immunized subcutaneously Results. Oral administration of beta-glucan significantly increased (two-fold) the antibody response to HA after immunization with each of the three commercially available vaccines (see Table 4), whether inactivated, partially purified or recombinant. The effect of beta-glucan on HI titers was consistent throughout the immunization period.

Summary of HAI titers of FluBlok, FluArix and Fluzone

TABLE 4

HAI titers
FluBlok Sera HAI titer

| | FluBlok | | | | | | FluBlok + BG | | | | | |
|---|---|---|---|---|---|---|---|---|---|---|---|---|
| | M1 | M2 | M3 | M4 | M4 | Median | M1 | M2 | M3 | M4 | M4 | Median |
| D14 | 40 | 40 | 40 | 40 | 80 | 40 | 40 | 80 | 80 | 80 | 80 | 80 |
| D21 | 160 | NT | 640 | 320 | 640 | 480 | 320 | 640 | 640 | 640 | 1280 | 640 |
| D28 | 320 | NT | 320 | 320 | 80 | 320 | 320 | 320 | 640 | 1280 | 1280 | 640 |

NT: Sera not available to test

FluArix sera HAI titer

| | FluArix | | | | | | FluArix + BG | | | | | |
|---|---|---|---|---|---|---|---|---|---|---|---|---|
| | M1 | M2 | M3 | M4 | M4 | Median | M1 | M2 | M3 | M4 | M4 | Median |
| D14 | 160 | 0 | 320 | 160 | 0 | 160 | 160 | 80 | 640 | 640 | 640 | 640 |
| D21 | 160 | 640 | 320 | 640 | 160 | 320 | 80 | 160 | 640 | 640 | 640 | 640 |
| D28 | 80 | 160 | 640 | 320 | 80 | 160 | 80 | 160 | 320 | 640 | 640 | 320 |
| D35 | 160 | 640 | 640 | 320 | 160 | 320 | 160 | 320 | 640 | 640 | 640 | 640 |

FluZone Sera HAI titer

| | FluBlok | | | | | | | FluBlok + BG | | | | | |
|---|---|---|---|---|---|---|---|---|---|---|---|---|---|
| | M1 | M2 | M3 | M4 | M5 | M6 | Median | M1 | M2 | M3 | M4 | M4 | Median |
| D14 | 160 | 20 | 0 | 20 | 40 | 0 | 20 | 40 | 40 | 40 | 0 | 0 | 40 |
| D21 | 320 | 320 | 320 | 640 | 640 | 640 | 480 | >640 | >640 | >640 | >640 | >640 | >640 |
| D28 | 160 | 160 | 160 | 160 | 640 | 80 | 160 | 160 | 640 | NT | 80 | 320 | 240 |
| D35 | 80 | 160 | 160 | 160 | 640 | 80 | 160 | 160 | 320 | 320 | 40 | 640 | 320 |

Accordingly, the yeast beta-glucans of the present technology are useful in methods for enhancing the immunogenicity of poorly immunogenic antigen-specific vaccines (e.g., inactivated, partially purified or recombinant HA) in a subject in need thereof.

Example 13: Evaluation of Oral Beta-glucan Induced Antibody Response with GD2L/GD3L-KLH conjugate or Fucosyl-GM1-KLH Constructs Experimental design. Animals were divided into the following experimental groups:

GD2/GD3-KLH vaccine treatment groups: (1) Oral beta-glucan alone; (2) GD2/GD3-KLH vaccine alone (subcutaneous); (3) GD2/GD3-KLH vaccine (subcutaneous) and oral Beta-glucan; (4) GD2/GD3-KLH vaccine mixed with QS-21 (subcutaneous); and (5) GD2/GD3-KLH vaccine mixed with QS-21 (subcutaneous) and oral beta-glucan.

Fucosyl GM1-KLH vaccine treatment groups: (1) Oral beta-glucan alone; (2) Fucosyl GM1-KLH vaccine alone (subcutaneous); (3) Fucosyl GM1-KLH vaccine (subcutaneous) and oral Beta-glucan; (4) Fucosyl GM1-KLH vaccine mixed with OPT-821 (subcutaneous); and (5) Fucosyl GM1-KLH vaccine mixed with OPT-821 (subcutaneous) and oral beta-glucan.

Figure 26:
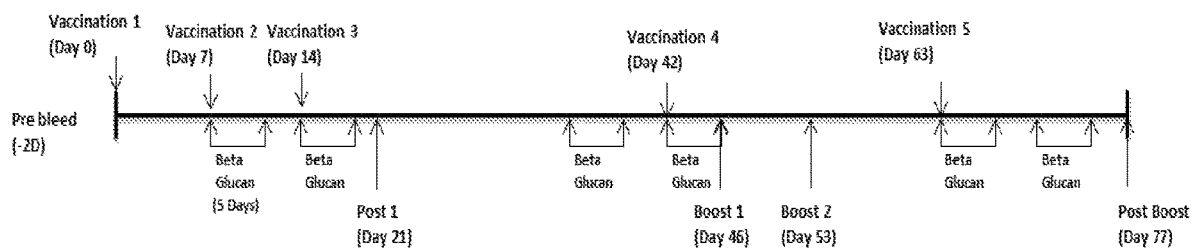
FIG. 26 shows the vaccination, gavage and bleeding schedule for administration of the GD2L/GD3L-KLH conjugate or Fucosyl-GM1-KLH conjugate vaccine.
Figure 27:
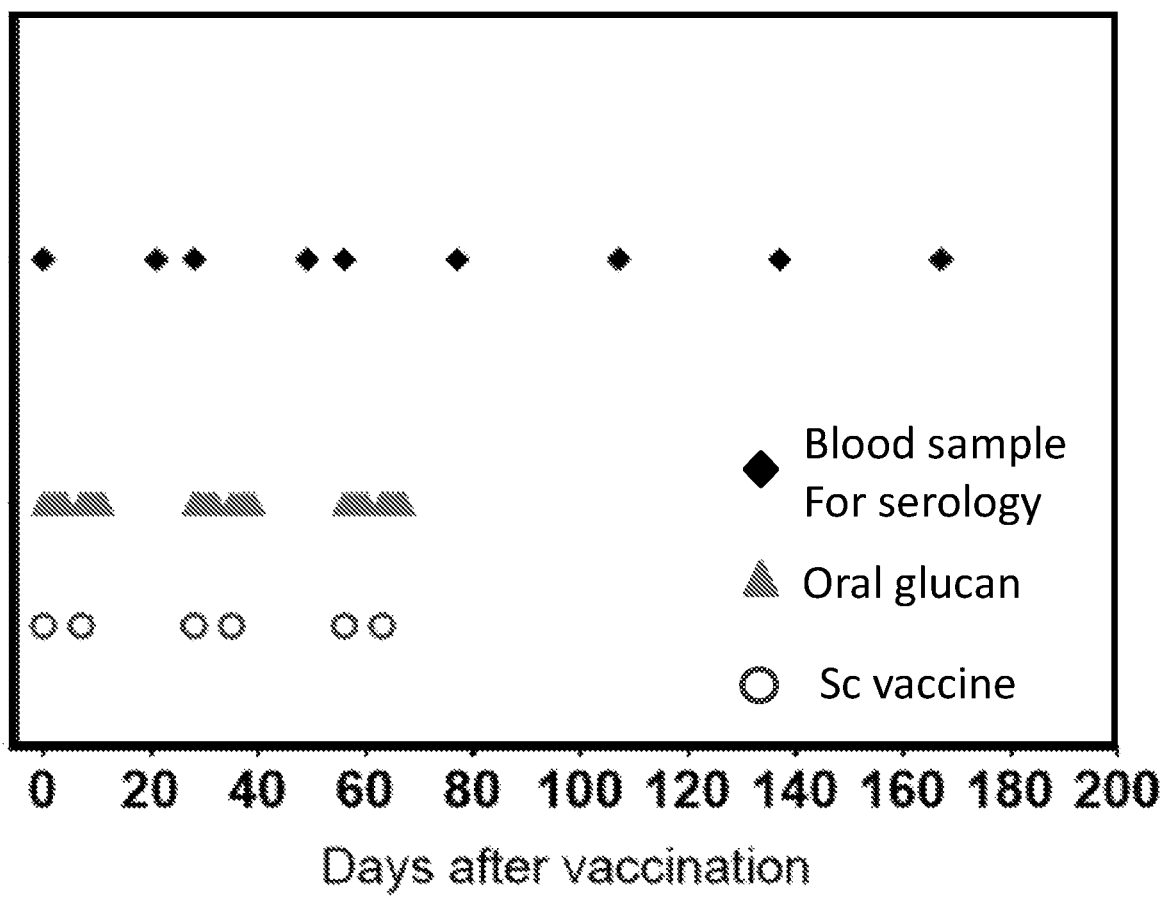
FIG. 27 shows the immunization schedule for administration of the GD2L/GD3L-KLH conjugate or Fucosyl-GM1-KLH conjugate vaccine.

Mice were vaccinated either with GD2/GD3-KLH (5 µg/mouse) or Fucosyl-GM1-KLH (5 µg/mouse)+QS-21 (20 µg/mouse) or OPT-821 (20 µg/mouse) on days 0, 7, 14, 42 and 63. A subset of the treatment groups received beta-glucan (40 mg/kg/mouse, 5 days a week) from days 7-11, days 14-18, days 35-39, days 42-46, days 63-67, and days 70-74. Mice vaccinated with vaccine alone, vaccine plus OPT-821 and beta-glucan alone served as control groups. A total of 5 bleeds were performed: 2 days prior to day 0, day 21, day 46, day 53, and day 77. The vaccination, gavage, bleeding, and immunization schedule are depicted in FIG. 26 and FIG. 27.

Evaluation of immune response by quantitative ELISA assay. Beads were coated with GD2 or Fucosyl GM1 at 0.2 µg/well in 60 µl of ethanol (incubated overnight in hood). ELISA plates were blocked with 1% HSA-PBS at room temperature for 1 hr. Sera were diluted at 1:40 with 0.5% HSA and assayed via ELISA. Mouse 3F8 and 3G6 were used as reference antibodies for ELISA quantification of IgG and IgM GD2 titers, respectively (two-fold dilution series from 5 µg/ml to 0.039 µg/ml). Mouse mAb F12 (µg/ml) was used as a reference for ELISA quantification of anti-FucGM1 antibody IgG titer. 100 µl of diluted sera or antibodies were added to each well accordingly, and incubated for 1-2 hrs at room temperature. AP-conjugated Goat Anti-Mouse IgG or IgM (secondary antibody) was diluted at 1:1000 with 0.5% HSA-PBS. 100 µl of diluted secondary antibody was added per well and incubated for 1 hr at room temperature. The wells were then incubated with p-Nitrophenyl Phosphate Substrate (Sigma-Aldrich, MO) for 30 min at room temperature, and the colorimetric results were read at 415 nM.

Figure 28:
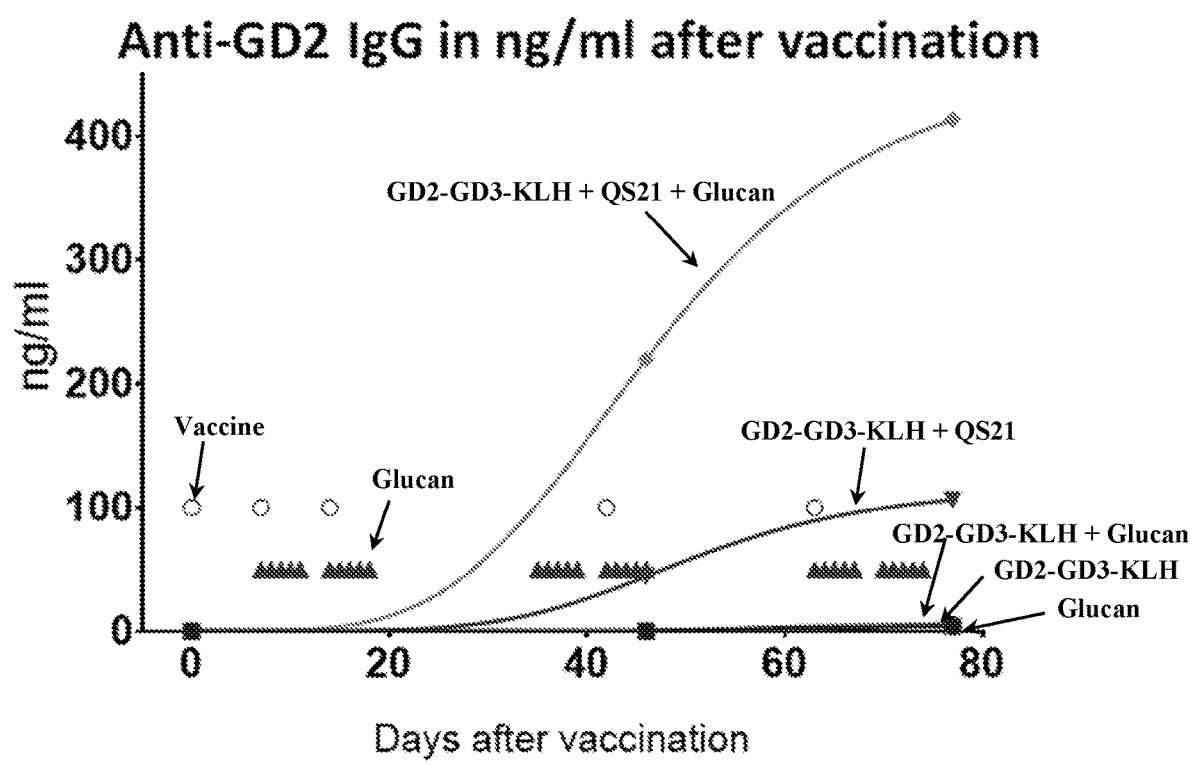
FIG. 28 shows the estimated anti-GD2 antibody IgG titer of mice vaccinated with GD2L/GD3L-KLH+OPT821 with or without beta Glucan. Mouse mAb 3F8 (µg/ml) was used as a reference for ELISA quantification.
Figure 29:
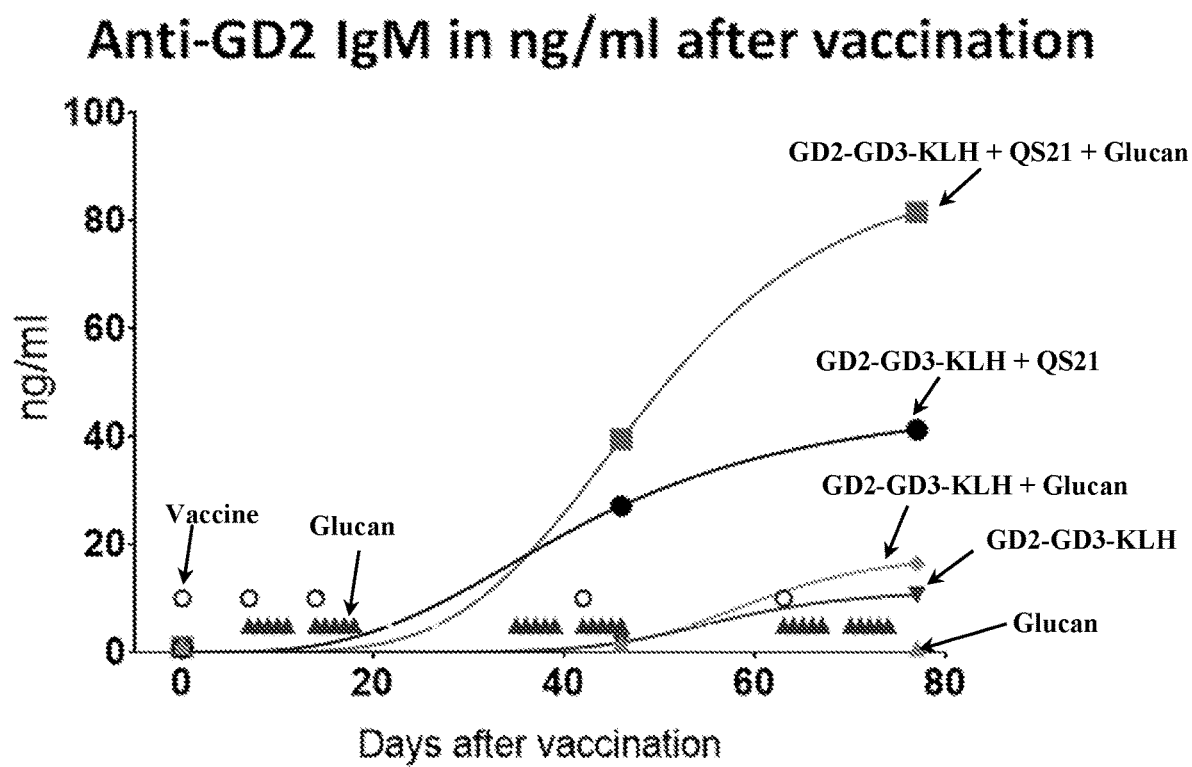
FIG. 29 shows the estimated anti-GD2 antibody IgM titer of mice vaccinated with GD2L/GD3L-KLH+OPT821 with or without beta Glucan. Mouse Ab 3G6 (µg/ml) was used as a reference for ELISA quantification.
Figure 30:
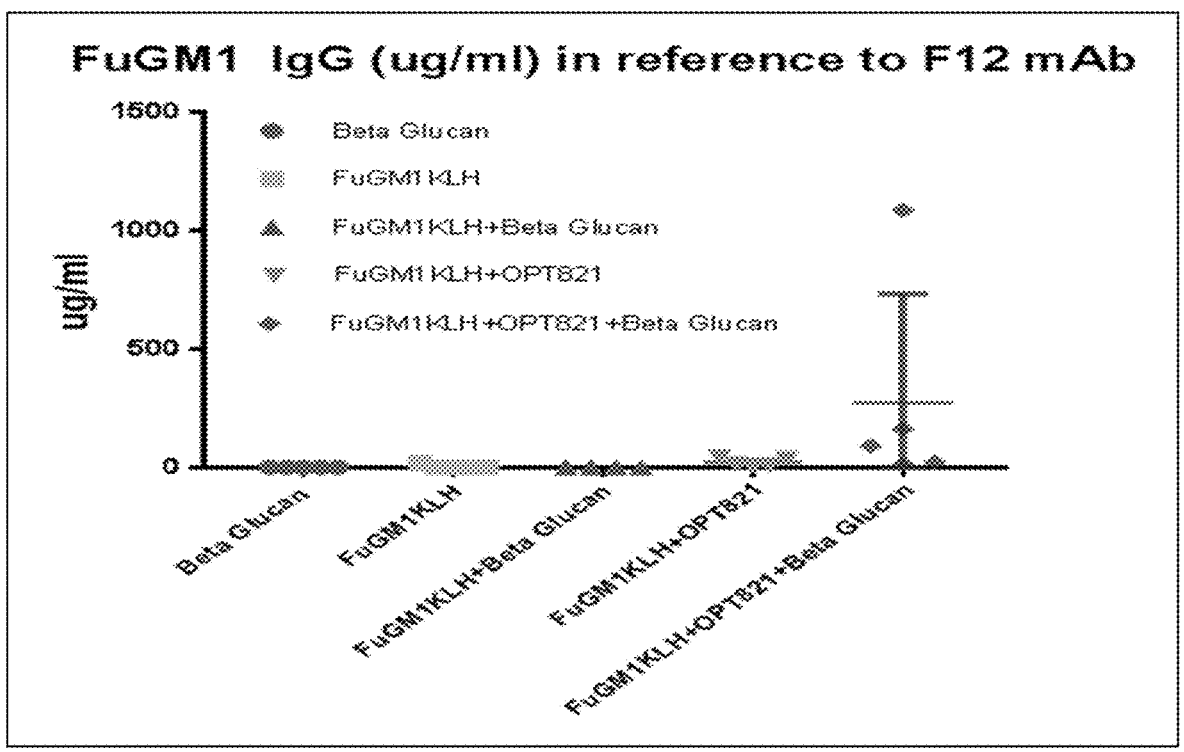
FIG. 30 shows the estimated anti-FucGM1 antibody IgG titer of mice vaccinated with FucGM1-KLH+OPT821 with or without beta Glucan. Mouse mAb F12 (µg/ml) was used as a reference for ELISA quantification.

As shown in FIG. 28 and FIG. 29, mice vaccinated with GD2L-KLH plus QS-21 and gavaged with beta-glucan showed a greater than 4-fold increase in IgG antibody titer and a greater than 2-fold increase in IgM antibody titer compared to mice that were only vaccinated with GD2L-KLH plus QS-21 adjuvant. Likewise, mice vaccinated with Fucosyl-GM1-KLH plus OPT-821 and gavaged with beta-glucan showed more than a 10-fold increase in IgG antibody titer relative to mice that were only vaccinated with Fucosyl-GM1-KLH plus OPT-821 adjuvant. See FIG. 30. These antibody titers are significantly higher than those reported in prior studies with Fucosyl GM1-KLH conjugate and GD2-

KLH vaccines. See Krug et al., Clinical Cancer Research 10:6094-6100 (2004); Cappello et al., Cancer Immunol Immunother 48:483-492 (1999); Dickler et al., Clinical Cancer Research 5:2773-2779 (1999); and Ragupathi et al., Clinical Cancer Research 9:5214-5220 (2003).

Accordingly, the yeast beta-glucans of the present technology are useful in methods for enhancing the immunogenicity of poorly immunogenic antigen-specific vaccines (e.g., GD2-KLH, GD3-KLH, or Fucosyl-GM1-KLH) in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for inducing therapeutic IgG antibody titer levels in response to a poorly immunogenic antigen-specific vaccine in a subject in need thereof comprising:
   (a) administering to the subject an effective amount of the poorly immunogenic antigen-specific vaccine, wherein the poorly immunogenic antigen-specific vaccine
   (i) comprises at least one poorly immunogenic antigen that is optionally linked to a carrier, wherein the at least one poorly immunogenic antigen is a peptide, a polypeptide, a carbohydrate, or a lipid; and
   (ii) is not a whole cell tumor vaccine; and
   (b) administering to the subject an effective amount of a yeast beta-glucan comprising a plurality of β-(1,3) side chains linked to a β-(1,3) backbone via β-(1,6) linkages, and wherein the yeast beta-glucan has a range of average molecular weights from about 6 kDa to about 30 kDa, and
   wherein administration of the poorly immunogenic antigen-specific vaccine and the yeast beta-glucan induces at least a 1.5-fold increase in therapeutic IgG antibody titer levels in the subject compared to a control subject that receives the poorly immunogenic antigen-specific vaccine without the yeast beta-glucan.

2. The method of claim 1, wherein the subject is an immunocompromised subject, a pediatric subject, a geriatric subject, or a subject that does not suffer from a disease or infection.

3. The method of claim 1, wherein the at least one poorly immunogenic antigen is a target antigen for a disease or infection, and wherein the target antigen is a peptide, a polypeptide, a nucleic acid, a carbohydrate, or a lipid.

4. The method of claim 3, wherein the disease or infection is selected from the group consisting of neurodegenerative disease, melanoma, neuroblastoma, glioma, small cell lung cancer, t-ALL, breast cancer, brain tumors, retinoblastoma, Ewing's sarcoma, osteosarcoma, ovarian cancer, non-Hodgkin's lymphoma, Epstein-Barr related lymphoma, Hodgkin's lymphoma, leukemia, epidermoid carcinoma, prostate cancer, renal cell carcinoma, transitional cell carcinoma, lung cancer, colon cancer, liver cancer, stomach cancer, gastrointestinal cancer, pancreatic cancer, HIV, tuberculosis, malaria, influenza, Ebola, chicken pox, Hepatitis B, HPV, tetanus, pneumococcus, measles, mumps, rubella, influenza, polio, diphtheria, tetanus, pertussis, Rous Sarcoma Virus, rabies, and rotavirus.

5. The method of claim 1, wherein the at least one poorly immunogenic antigen is inactivated, partially purified or recombinant hemagglutinin (HA) protein or fucosyl GM1.

6. The method of claim 1, wherein the carrier is keyhole limpet hemocyanin (KLH).

7. The method of claim 1, wherein the poorly immunogenic antigen-specific vaccine and the yeast beta-glucan are administered separately, sequentially or simultaneously.

8. The method of claim 1, wherein the poorly immunogenic antigen-specific vaccine or the yeast beta-glucan is administered intravenously, intramuscularly, intraarterially, intrathecally, intracapsularly, intraorbitally, intradermally, intraperitoneally, transtracheally, subcutaneously, intracerebroventricularly, orally or intranasally.

9. The method of claim 1, wherein administration of the poorly immunogenic antigen-specific vaccine and the yeast beta-glucan results in a 10-fold increase in therapeutic IgG antibody titer levels in the subject compared to that observed in the subject prior to administration of the poorly immunogenic antigen-specific vaccine and the yeast beta-glucan.

10. The method of claim 1, wherein the subject has been exposed to chemoradiotherapy.

11. The method of claim 1, wherein the subject exhibits persistent therapeutic IgG antibody titer levels following the administration of both the poorly immunogenic antigen-specific vaccine and the yeast beta-glucan.

12. The method of claim 4, wherein the neurodegenerative disease is Alzheimer's disease.

\* \* \* \* \*